United States Patent
Billen et al.

(10) Patent No.: US 9,200,003 B2
(45) Date of Patent: Dec. 1, 2015

(54) CRYSTALLINE FORMS OF 1-(5'-(5-(3,5-DICHLORO-4-FLUOROPHENYL)-5-(TRIFLUORO-METHYL)-4,5-DIHYDROISOXAZOL-3-YL)-3'H-SPIRO[AZETIDINE-3,1'-ISOBENZOFURAN]-1-YL)-2-(METHYLSULFONYL) ETHANONE

(71) Applicant: Zoetis Services LLC, Florham Park, NJ (US)

(72) Inventors: Denis Billen, Kalamazoo, MI (US); Matthew Joseph Birchmeier, Kalamazoo, MI (US); Ronald J. VanderRoest, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/422,098

(22) PCT Filed: Aug. 28, 2013

(86) PCT No.: PCT/US2013/056945
§ 371 (c)(1),
(2) Date: Feb. 17, 2015

(87) PCT Pub. No.: WO2014/036056
PCT Pub. Date: Mar. 6, 2014

(65) Prior Publication Data
US 2015/0183795 A1    Jul. 2, 2015

Related U.S. Application Data

(60) Provisional application No. 61/695,410, filed on Aug. 31, 2012.

(51) Int. Cl.
*C07D 491/107* (2006.01)
*A61K 31/422* (2006.01)
*A61K 45/06* (2006.01)

(52) U.S. Cl.
CPC .......... *C07D 491/107* (2013.01); *A61K 31/422* (2013.01); *A61K 45/06* (2013.01); *C07B 2200/13* (2013.01)

(58) Field of Classification Search
None
See application file for complete search history.

(56) References Cited

U.S. PATENT DOCUMENTS 8,466,115 B2 * 6/2013 Curtis et al. .................... 514/30

FOREIGN PATENT DOCUMENTS

| WO | 2010/084067 | 7/2010 |
| WO | 2011/104089 | 9/2011 |
| WO | 2012/120399 | 9/2012 |

OTHER PUBLICATIONS

PCT International Search Report, PCT/US2013/056945 filed Aug. 28, 2013 (3 pages).

* cited by examiner

*Primary Examiner* — Michael Barker
(74) *Attorney, Agent, or Firm* — Paul M. Misiak; Barbara L. Renda

(57) ABSTRACT

The present invention relates to novel crystalline modifications of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone. The present invention also describes compositions and methods of treating a parasitic infection or infestation in an animal in need thereof. The present invention also relates to processes for making the crystalline forms.

20 Claims, 7 Drawing Sheets

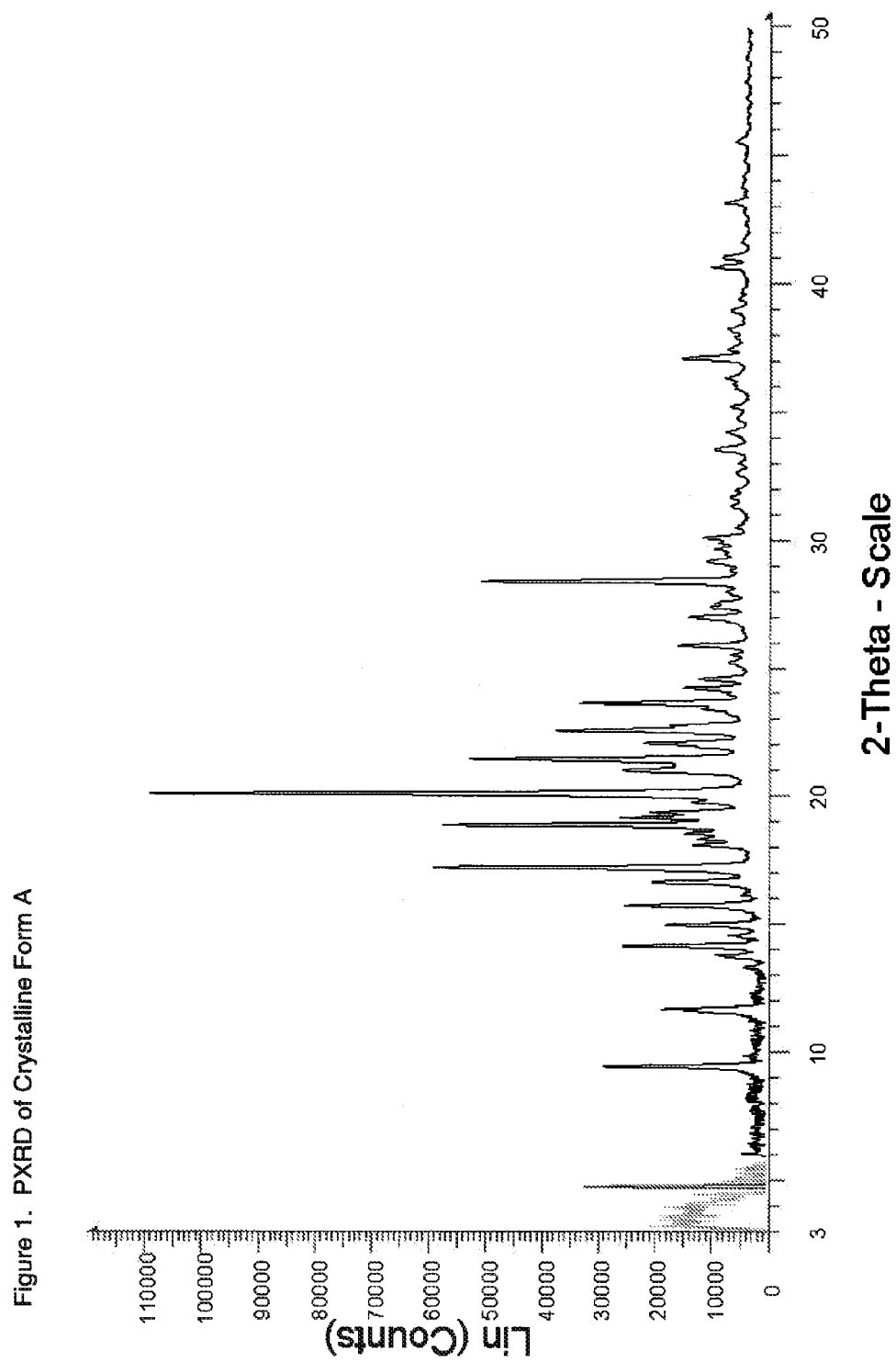
Figure 1. PXRD of Crystalline Form A

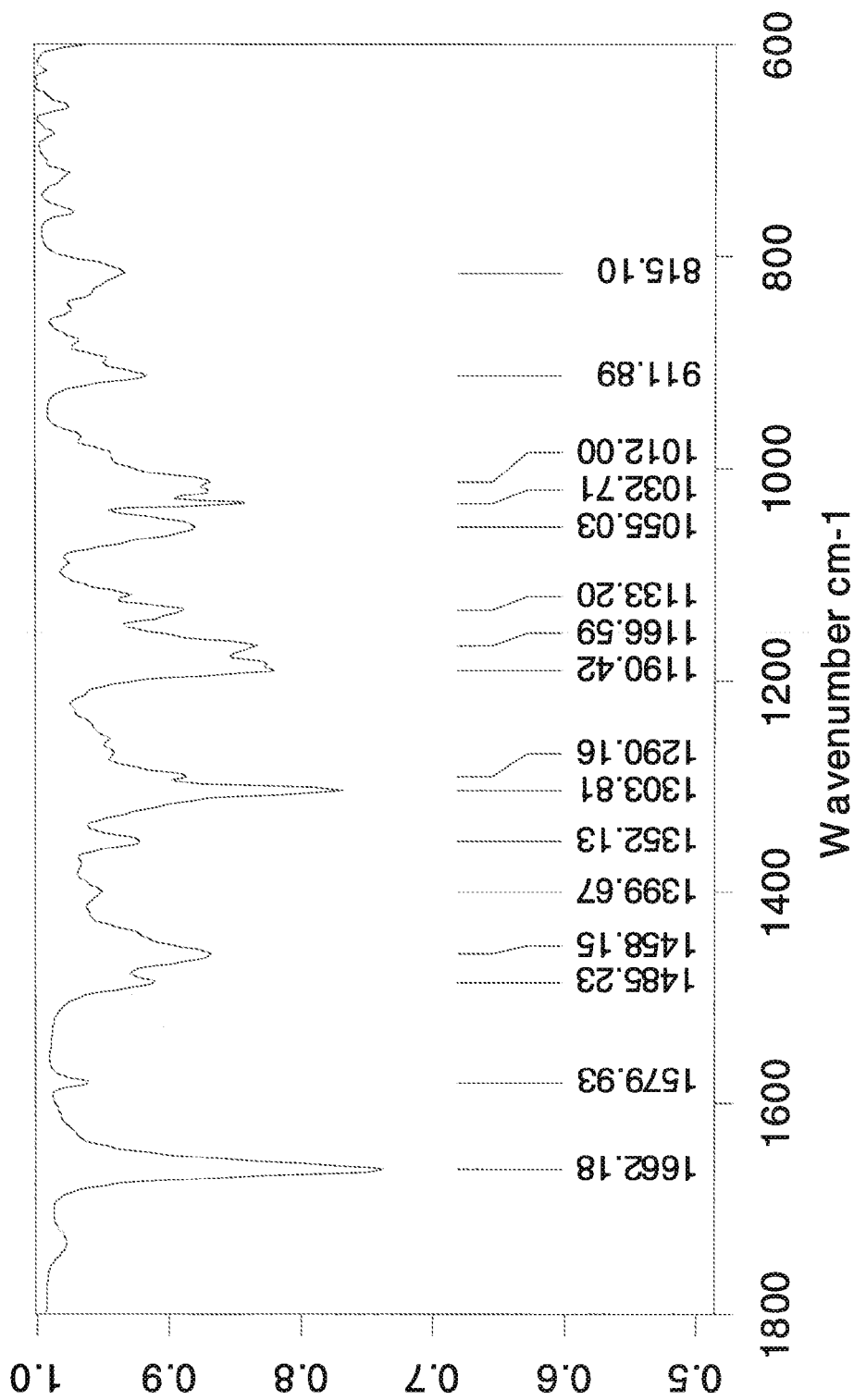
Figure 2. FT-IR of Crystalline Form A

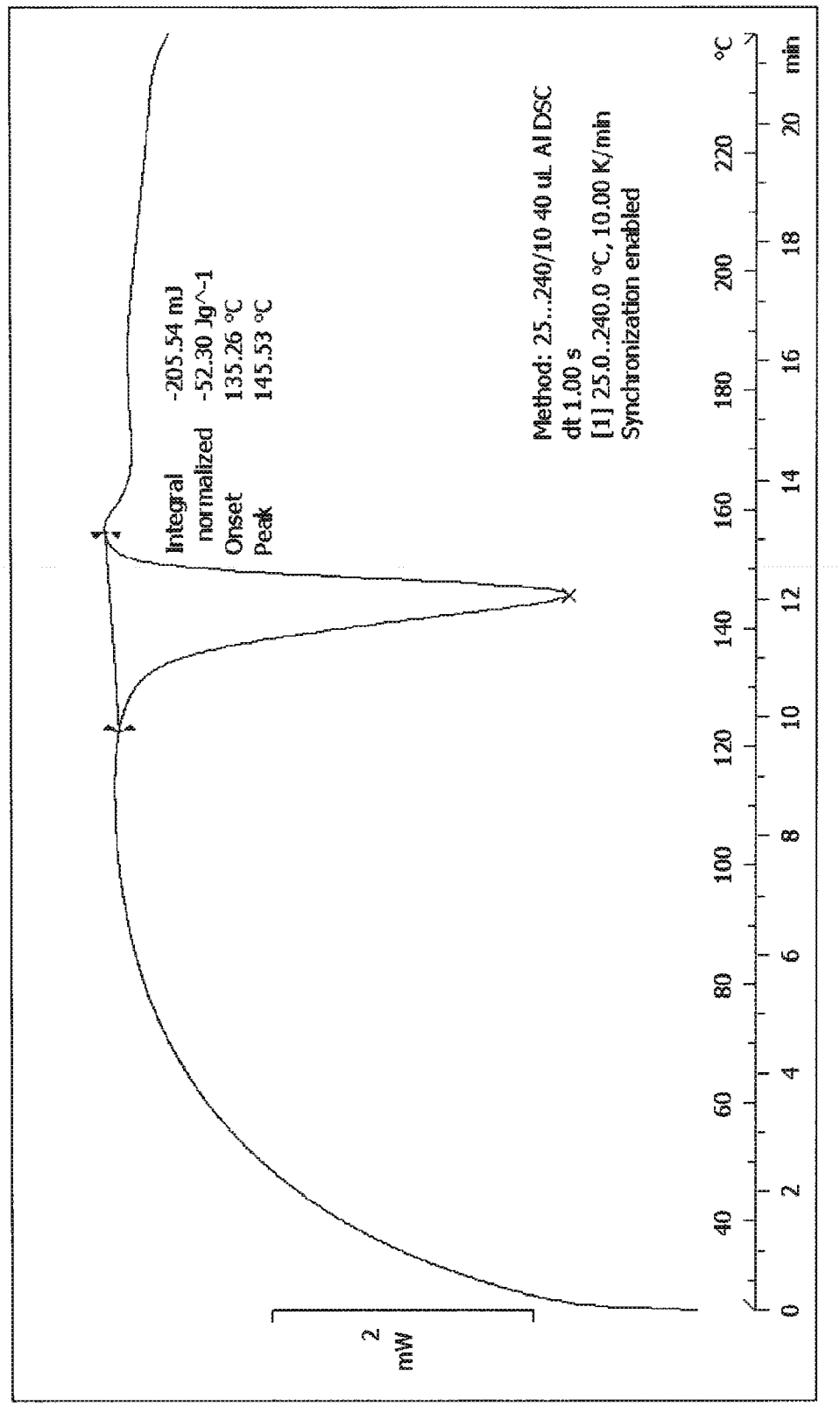
Figure 3.1. DSC of Crystalline Form A

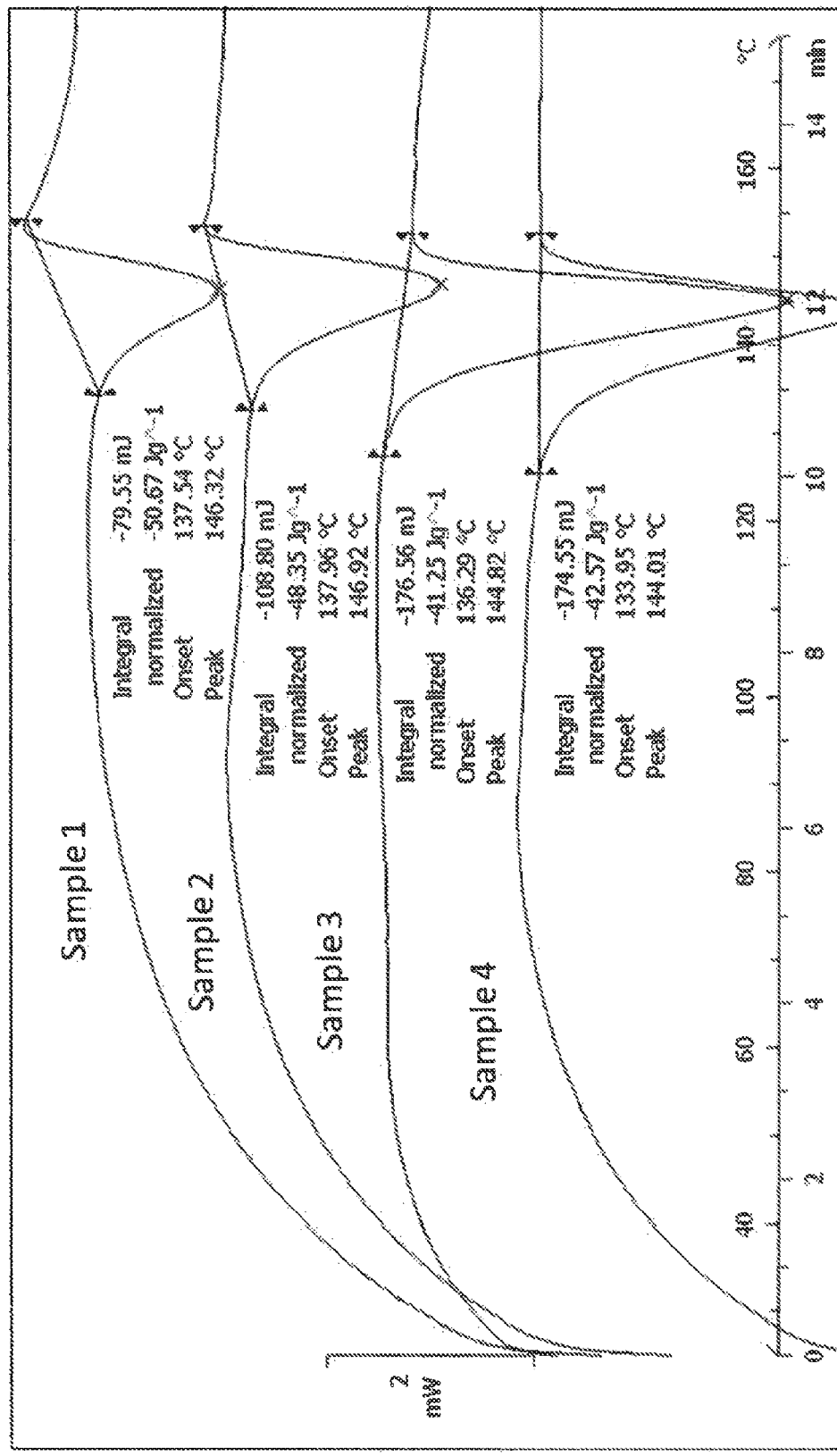
Figure 3.2. DSC of Multiple Lots of Crystalline Form A

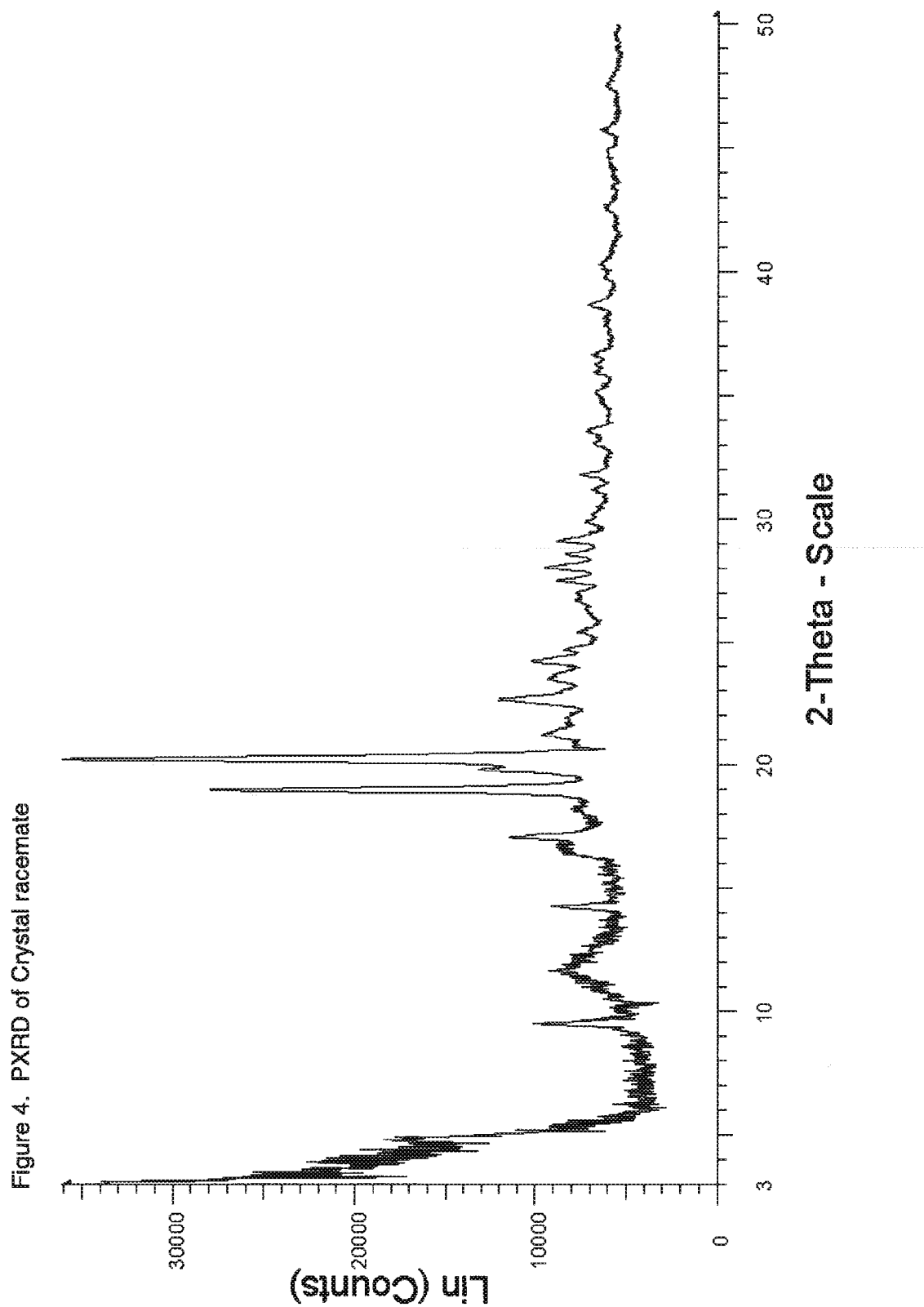
Figure 4. PXRD of Crystal racemate

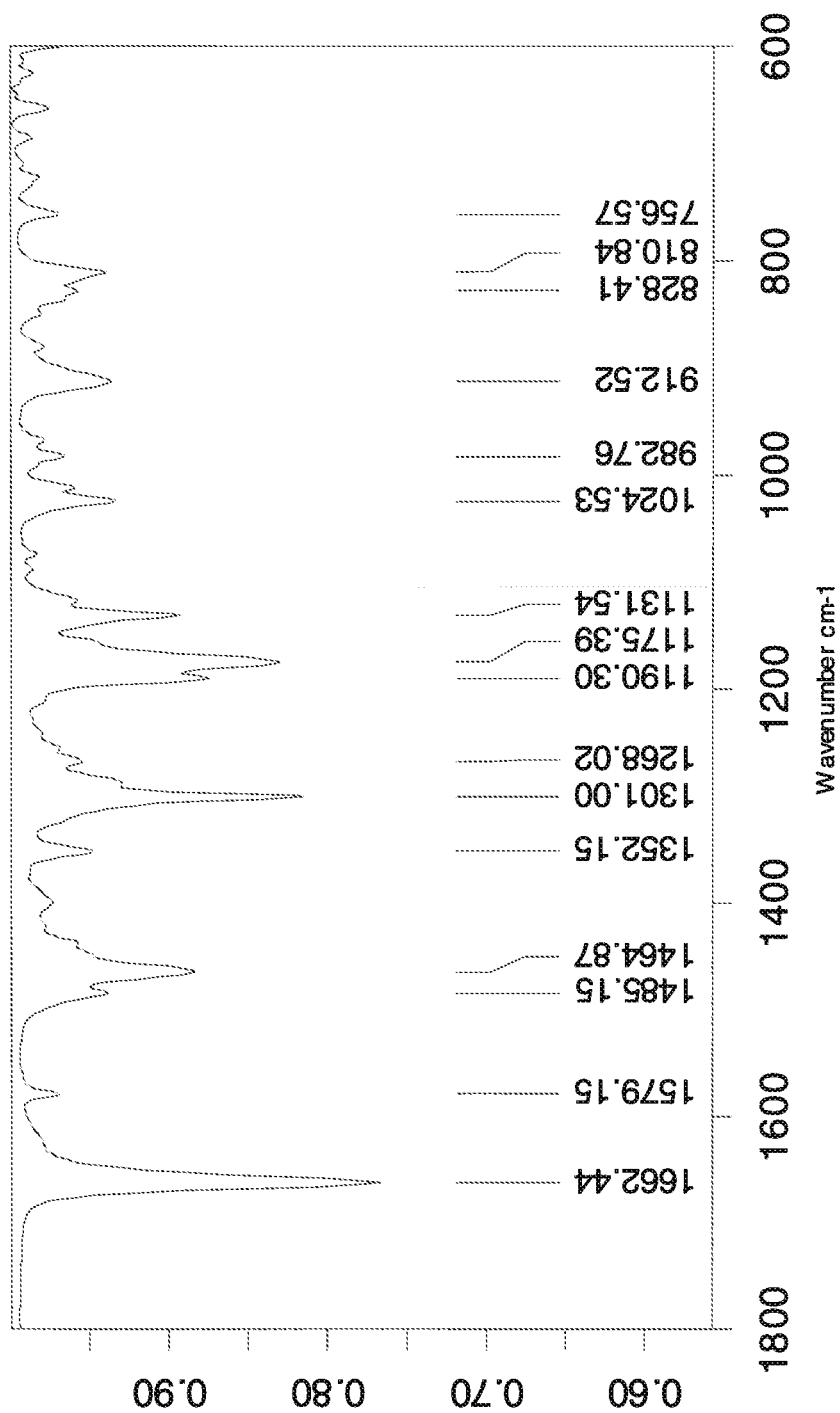
Figure 5. FTIR of the Crystal racemate

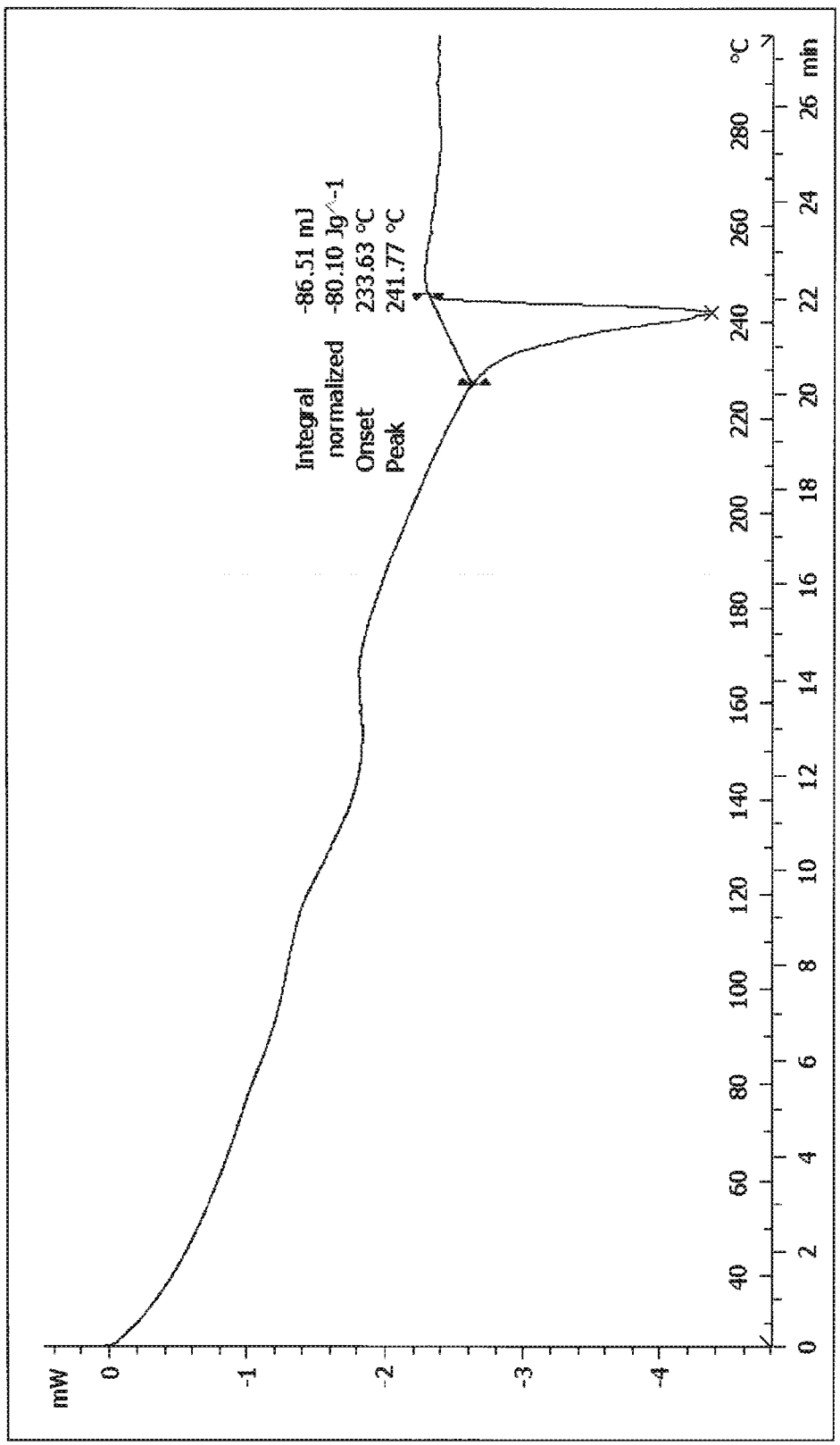
Figure 6. DSC of the Crystal racemate

CRYSTALLINE FORMS OF 1-(5'-(5-(3,5-DICHLORO-4-FLUOROPHENYL)-5-(TRIFLUORO-METHYL)-4,5-DIHYDROISOXAZOL-3-YL)-3'H-SPIRO[AZETIDINE-3,1'-ISOBENZOFURAN]-1-YL)-2-(METHYLSULFONYL) ETHANONE

FIELD OF INVENTION

The present invention relates to novel crystalline forms of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, particularly Form A, to processes for the preparation of same, to compositions comprising said crystalline forms, and to the use of said crystalline forms as a parasiticidal agent for the treatment of animals in need thereof. The present invention also contemplates the use of the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone prepared from Form A for compositions and methods of use thereof, as an antiparasitic agent.

BACKGROUND OF THE INVENTION

The chiral compound 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone has the following structure: Formula (1), which is herein also referred to as Compound 1. The "*" represents the chiral carbon.

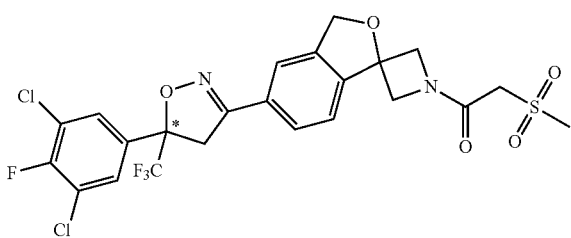

(1)

Compound 1 and its preparation are described in WO2012/120399 (which is herein incorporated in its entirety), Example 9. The WO publication further discloses that the Formula (1) compound is chiral and that it can be used as a parasiticide for use in treating animals with a parasitic infection or infestation. In the multistep process, the compound was liberated as a precipitant comprising about 90% of the amorphous S-enantiomer and about 10% of the amorphous R-enantiomer. The amorphous S-enantiomer was obtained by precipitating out equimolar amounts of the S- and R-enantiomers, i.e., the racemate. Further, the racemate was separated by chiral HPLC. The S- and R-enantiomers obtained from the preparations were characterized by HPLC (elution time), 1H-NMR analysis, and mass spectrometry.

If a compound is to be developed as a pharmaceutical or veterinary agent, it is important to provide a form of that compound (commonly known as a drug substance or active pharmaceutical/veterinary ingredient/agent) which can be reliably prepared and purified on a large scale and which does not degrade upon storage. A crystalline, and preferably a high-melting form of the compound is therefore desirable since high-melting point crystalline solids tend to be easy to purify by crystallization and are more stable than the non-crystalline (amorphous) form.

The crystalline forms of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone have not been previously described or characterized.

Different solid-state forms of a pharmaceutical or veterinary compound can have materially different physical properties. Such differences in physical properties can have an impact, for example, on how a pharmaceutical or veterinary compound is made, processed, formulated or administered. For example, the crystalline form of one compound may have very different properties: solubility, rate of dissolution, suspension stability, stability during grinding, vapor pressure, optical and mechanical properties, hygroscopicity, crystal size, filtration properties, desiccation, density, melting point, degradation stability, stability against phase transformation into other crystalline forms, color, and even chemical reactivity. Accordingly, the identification of new solid-state forms (i.e., crystalline forms or polymorphs) of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone that provide an advantage relative to other solid-state forms in making, processing, formulating, or administering the compound are desirable.

As described, the solid state chiral Compound 1 is about 90:10 (S:R) when synthesized. Separation of the solid state (crystal) racemate (equimolar portions of the S- and R-enantiomers) results in almost pure amorphous S-enantiomer, about 80% of the originally synthesized compound, which can then be readily crystallized, in an almost pure (~97+%) crystal state. The S- and R-enantiomers of the racemate can be further separated by chiral HPLC and crystallized.

When crystallized, each of the S- and R-enantiomers of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone form a single anhydrous crystalline form. The crystalline form of the S-enantiomer is designated as Form A. The crystalline form of the R-enantiomer is similar to that of Form A and the solid state crystalline form of the S/R racemate is designated as the "crystalline racemate".

SUMMARY OF THE INVENTION

The present invention relates to novel crystalline forms of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (i.e., Formula 1; Compound 1) shown below,

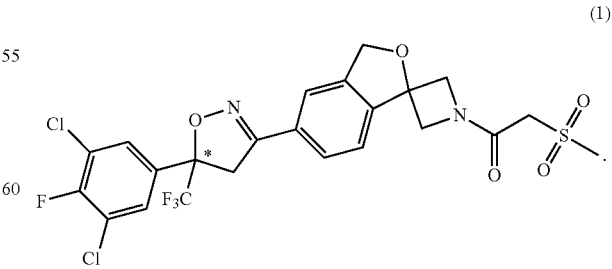

(1)

The "*" represents the chiral carbon.

In one aspect of the present invention, is the crystalline Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone.

In another aspect of the present invention, is the crystalline form of (R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, which is a similar crystal form to that of Form A (S-enantiomer).

In another aspect of the present invention, is the crystalline form of the racemate, (S/R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone.

In another aspect of the present invention, is the amorphous S-enantiomer of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystal Form A.

In another aspect of the present invention is the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, compositions thereof, and methods of use to treat a parasitic infection and infestation in an animal in need thereof.

In a preferred aspect, the invention provides specific crystalline forms of Compound 1. Each of these crystalline forms has a unique three-dimensional crystalline configuration that can be characterized by, inter alia, the way the crystal lattice diffracts electromagnetic radiation (e.g., powder X-ray diffraction (PXRD or pxrd) and Fournier-transform infrared (FT-IR) spectroscopy), and its melting characteristics (e.g., differential scanning calorimetry (DSC)). For convenience, each of these crystalline forms has been allocated a descriptor for characterization, though these descriptors have no inherent technical significance. As described herein, the crystal forms of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, include Form A which crystallizes from the S-enantiomer, and the solid state crystal form of the racemate. The crystalline form of the R-enantiomer is similar to that of Form A. Form A is the preferred crystalline form of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone.

Form A exhibits a powder X-ray diffraction pattern substantially as shown in FIG. 1. The characteristic peaks of Form A expressed in degrees 2θ [2-Theta°] (±0.2°), interplanar spacings (d-spacing), and respective intensities (%) are displayed in Table 1 below. One skilled in the art will recognize that intensities of the peaks in the diffractogram are a function of the orientation of the crystals in the sample, so physical modifications such as milling or hand grinding, or crystallization from a different solvent, may affect the intensity of the peaks, while their position remains unchanged, for the same crystal form.

TABLE 1

PXRD of Crystalline Form A

| Peak | 2-Theta° | d-spacing | Intensity (%) |
|---|---|---|---|
| 1 | 3.98 | 22.16 | 3.3 |
| 2 | 4.25 | 20.76 | 3.0 |
| 3 | 4.70 | 18.79 | 38.8 |
| 4 | 5.13 | 17.20 | 7.2 |
| 5 | 5.24 | 16.84 | 6.5 |
| 6 | 5.52 | 15.99 | 7.3 |
| 7 | 5.98 | 14.76 | 16.6 |
| 8 | 9.39 | 9.42 | 36.1 |
| 9 | 11.61 | 7.62 | 28.0 |
| 10 | 13.26 | 6.67 | 16.4 |
| 11 | 13.72 | 6.45 | 20.4 |
| 12 | 14.10 | 6.28 | 33.4 |
| 13 | 14.52 | 6.10 | 18.5 |
| 14 | 14.94 | 5.92 | 27.4 |
| 15 | 15.70 | 5.64 | 33.3 |
| 16 | 16.13 | 5.49 | 16.4 |
| 17 | 16.60 | 5.34 | 29.2 |
| 18 | 17.18 | 5.16 | 60.0 |
| 19 | 18.06 | 4.91 | 23.4 |
| 20 | 18.29 | 4.85 | 22.9 |
| 21 | 18.51 | 4.79 | 24.7 |
| 22 | 18.83 | 4.71 | 58.8 |
| 23 | 19.12 | 4.64 | 33.7 |
| 24 | 19.32 | 4.59 | 29.6 |
| 25 | 19.72 | 4.50 | 23.7 |
| 26 | 20.07 | 4.42 | 100 |
| 27 | 20.97 | 4.23 | 33.3 |
| 28 | 21.42 | 4.14 | 55.1 |
| 29 | 22.03 | 4.03 | 30.5 |
| 30 | 22.54 | 3.94 | 42.8 |
| 31 | 22.76 | 3.90 | 26.1 |
| 32 | 23.62 | 3.76 | 39.5 |
| 33 | 24.21 | 3.67 | 24.9 |
| 34 | 24.61 | 3.61 | 22.7 |
| 35 | 25.26 | 3.52 | 18.5 |
| 36 | 25.91 | 3.44 | 25.6 |
| 37 | 27.01 | 3.30 | 24.2 |
| 38 | 27.57 | 3.23 | 20.5 |
| 39 | 28.02 | 3.18 | 18.9 |
| 40 | 28.42 | 3.14 | 53.5 |
| 41 | 29.20 | 3.06 | 21.7 |
| 42 | 29.69 | 3.01 | 20.6 |
| 43 | 30.13 | 2.96 | 22.2 |
| 44 | 31.36 | 2.85 | 18.2 |
| 45 | 31.70 | 2.82 | 18.3 |
| 46 | 32.65 | 2.74 | 17.4 |
| 47 | 33.59 | 2.67 | 20.6 |
| 48 | 34.25 | 2.62 | 19 |
| 49 | 35.24 | 2.54 | 18.4 |
| 50 | 36.35 | 2.47 | 19 |
| 51 | 37.13 | 2.42 | 25 |
| 52 | 37.51 | 2.40 | 18.6 |
| 53 | 38.27 | 2.35 | 18.7 |
| 54 | 39.01 | 2.31 | 18.3 |
| 55 | 40.69 | 2.22 | 21 |
| 56 | 41.08 | 2.20 | 19.4 |
| 57 | 43.2 | 2.09 | 19 |
| 58 | 45.59 | 1.99 | 17.5 |

In another aspect of the present invention, crystal Form A has characteristic PXRD peaks expressed in degrees 2θ (±0.2°) at about one or more of the following positions: 4.70, 9.39, 14.10, 15.70, 17.18, 18.83, 19.12, 20.07, 20.97, 21.42, 22.03, 22.54, 23.62, and 28.42, all of which have a relative intensity of at least 30%. In another aspect of the present invention, crystal Form A has characteristic PXRD peaks expressed in degrees 2θ (±0.2°) at about one or more of the following positions: 17.18, 18.83, 20.07, 21.42, 22.54, and 28.42, all of which have a relative intensity of at least 40%. In another aspect of the present invention, crystal Form A has characteristic PXRD peaks expressed in degrees 2θ (±0.2°) at about one or more of the following positions: 17.18, 18.83, 20.07, 21.42, and 28.42, all of which have a relative intensity of at least 50%. In yet another aspect of the present invention, crystal Form A has characteristic PXRD peaks expressed in degrees 2θ (±0.2°) at about one or more of the following positions: 17.18, 18.83, and 20.07, all of which have a relative intensity of at least 58%. In another aspect of the present invention, crystal Form A has characteristic PXRD peaks expressed in degrees 2θ (±0.20) at about the following positions: 17.18, 18.83, and 20.07. In another aspect of the present invention, crystal Form A has characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 4.70, 9.39, 14.10, 15.70, 19.12, 20.97, 22.03, 21.42, 22.54, 23.62, and 28.42. In another aspect of the present invention, crystal Form A has characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 21.42 and 28.42. In another aspect of the present invention, crystal Form A has characteristic PXRD peaks expressed in degrees 2θ (±0.2°) at about the following positions: 17.18, 18.83, 20.07, and 21.42. In another aspect of the present invention, crystal Form A has characteristic PXRD peaks expressed in degrees 2θ (±0.2°) at about the following positions: 17.18, 18.83, 20.07, and 28.42. In another aspect of the present invention, crystal Form A has characteristic PXRD peaks expressed in degrees 2θ (±0.2°) at about the following positions: 17.18, 18.83, 20.07, 21.42, and 28.42. In another aspect of the present invention, crystal Form A has characteristic PXRD peaks expressed in degrees 2θ (±0.2°) at about the following positions: 17.18, 18.83, 20.07, 21.42, 22.54, and 28.42. In another aspect of the present invention, crystal Form A has characteristic PXRD peaks expressed in degrees 2θ (±0.2°) at about the following positions: 17.18, 18.83, 20.07, 21.42, 22.54, and 28.42, further comprising at least one additional diffraction peak expressed in degrees 2θ (±0.2°) selected from the group consisting of peaks at about 4.70, 9.39, 14.10, 15.70, 19.12, 20.97, 22.03, and 23.62. In another aspect of the present invention, crystal Form A has characteristic PXRD peaks expressed in degrees 2θ (±0.2°) at about the following positions: 17.18, 18.83, 20.07, 21.42, 22.54, 23.62, and 28.42. In another aspect of the present invention, crystal Form A has characteristic PXRD peaks expressed in degrees 2θ (±0.2°) at about the following positions: 4.70, 17.18, 18.83, 20.07, 21.42, 22.54, 23.62, and 28.42. In another aspect of the present invention, crystal Form A has characteristic PXRD peaks expressed in degrees 2θ (±0.2°) at about the following positions: 4.70, 9.39, 17.18, 18.83, 20.07, 21.42, 22.54, 23.62, and 28.42. In another aspect of the present invention, crystal Form A has characteristic PXRD peaks expressed in degrees 2θ (±0.2°) at about the following positions: 4.70, 9.39, 17.18, 18.83, 19.12, 20.07, 21.42, 22.54, 23.62, and 28.42. In another aspect of the present invention, crystal Form A has characteristic PXRD peaks expressed in degrees 2θ (±0.2°) at about the following positions: 4.70, 9.39, 14.10, 17.18, 18.83, 19.12, 20.07, 21.42, 22.54, 23.62, and 28.42. In another aspect of the present invention, crystal Form A has characteristic PXRD peaks expressed in degrees 2θ (±0.2°) at about the following positions: 4.70, 9.39, 14.10, 15.70, 17.18, 18.83, 19.12, 20.07, 21.42, 22.54, 23.62, and 28.42. In another aspect of the present invention, crystal Form A has characteristic PXRD peaks expressed in degrees 2θ (±0.2°) at about the following positions: 4.70, 9.39, 14.10, 15.70, 17.18, 18.83, 19.12, 20.07, 20.97, 21.42, 22.54, 23.62, and 28.42. In another aspect of the present invention, crystal Form A has characteristic PXRD peaks expressed in degrees 2θ (±0.2°) at about the following positions: 4.70, 9.39, 14.10, 15.70, 17.18, 18.83, 19.12, 20.07, 20.97, 21.42, 22.03, 22.54, 23.62, and 28.42.

In another aspect of the present invention, crystal Form A also exhibits a Fournier-Transform Infrared (FT-IR) spectrum at the 1800 to 600 cm$^{-1}$ range substantially as shown in FIG. 2. Characteristic FT-IR peaks of Form A are shown in Table 2 below.

TABLE 2

FT-IR of Crystalline Form A

| Peak (cm$^{-1}$) | Absolute Intensity | Relative Intensity | Width |
| --- | --- | --- | --- |
| 1662 | −0.400 | 0.482 | 15.26 |
| 1459 | −0.148 | 0.219 | 26.81 |
| 1352 | −0.048 | 0.100 | 10.85 |
| 1304 | −0.432 | 0.523 | 11.36 |
| 1191 | −0.334 | 0.390 | 37.15 |
| 1166 | −0.285 | 0.075 | 7.49 |
| 1133 | −0.164 | 0.148 | 13.91 |
| 1023 | −0.118 | 0.189 | 22.58 |
| 984 | −0.011 | 0.065 | 13.26 |
| 912 | −0.180 | 0.258 | 17.62 |
| 815 | −0.131 | 0.199 | 36.74 |
| 757 | −0.046 | 0.117 | 10.61 |
| 721 | −0.025 | 0.085 | 14.90 |
| 659 | −0.043 | 0.130 | 9.62 |
| 625 | −0.018 | 0.081 | 12.07 |

In another aspect of the present invention, crystal Form A exhibits characteristic FT-IR peaks at the 1800 to 600 cm$^{-1}$ spectrum range at one or more of the following: 1662, 1459, 1352, 1304, 1191, 1166, 1133, 1023, 984, 912, 815, 757, 721, 659, and 625 cm$^{-1}$.

In another aspect of the present invention, crystal Form A exhibits characteristic FT-IR peaks at the 1800 to 600 cm$^{-1}$ spectrum range at one or more of the following: 1662, 1459, 1352, 1304, 1191, 1166, 1133, 1023, 984, 912, 815, 757, 721, 659, and 625 cm$^{-1}$, and has characteristic PXRD peaks expressed in degrees 2θ (±0.2°) at about one or more of the following positions: 4.70, 9.39, 14.10, 15.70, 17.18, 18.83, 19.12, 20.07, 20.97, 21.42, 22.03, 22.54, 23.62, and 28.42.

In another aspect of the present invention, crystal Form A exhibits characteristic FT-IR peaks at the 1800 to 600 cm$^{-1}$ spectrum range at one or more of the following: 1662, 1459, 1352, 1304, 1191, 1166, 1133, 1023, 984, 912, 815, 757, 721, 659, and 625 cm$^{-1}$, and has characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 4.70, 9.39, 14.10, 15.70, 19.12, 20.97, 22.03, 21.42, 22.54, 23.62, and 28.42. In another aspect of the present invention, crystal Form A exhibits characteristic FT-IR peaks at the 1800 to 600 cm$^{-1}$ spectrum range at one or more of the following: 1662, 1459, 1352, 1304, 1191, 1166, 1133, 1023, 984, 912, 815, 757, 721, 659, and 625 cm$^{-1}$, and has characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 21.42 and 28.42. In another aspect of the present invention, crystal Form A exhibits characteristic FT-IR peaks at the 1800 to 600 cm$^{-1}$ spectrum range at one or more of the following: 1662, 1459, 1352, 1304, 1191, 1166, 1133, 1023, 984, 912, 815, 757, 721, 659, and 625 cm$^{-1}$, and has characteristic PXRD peaks expressed in degrees 2θ (±0.2°) at about the following positions: 17.18, 18.83, 20.07, 21.42, and 28.42. In another aspect of the present invention, crystal Form A exhibits characteristic FT-IR peaks at the 1800 to 600 cm$^{-1}$ spectrum range at one or more of the following:

1662, 1459, 1352, 1304, 1191, 1166, 1133, 1023, 984, 912, 815, 757, 721, 659, and 625 cm$^{-1}$, and has characteristic PXRD peaks expressed in degrees 2θ (±0.2°) at about the following positions: 17.18, 18.83, 20.07, 21.42, 22.54, and 28.42. In another aspect of the present invention, crystal Form A exhibits characteristic FT-IR peaks at the 1800 to 600 cm$^{-1}$ spectrum range at one or more of the following: 1662, 1459, 1352, 1304, 1191, 1166, 1133, 1023, 984, 912, 815, 757, 721, 659, and 625 cm$^{-1}$, and has characteristic PXRD peaks expressed in degrees 2θ (±0.2°) at about the following positions: 17.18, 18.83, 20.07, 21.42, 22.54, and 28.42, and further comprising at least one additional diffraction peak expressed in degrees 2θ (±0.2°) selected from the group consisting of peaks at about 4.70, 9.39, 14.10, 15.70, 19.12, 20.97, 22.03, and 23.62.

In another aspect of the present invention, crystal Form A also exhibits a differential scanning calorimetry (DSC) thermogram substantially as shown in FIG. 3.1, which is characterized by a predominant endotherm peak at about 145.53° C. In another aspect of the present invention, crystal Form A also exhibits a DSC thermogram substantially as shown in FIG. 3.1, which is characterized by a predominant endotherm peak at about 145.53° C. with an onset of the endotherm at about 135.26° C.

In another aspect of the present invention, crystal Form A also exhibits a DSC thermogram substantially as shown in FIG. 3.2, which displays four different crystalline Form A samples, which is characterized by a predominant endotherm peak at about 144.01, 144.82, 146.32, and 146.92° C. with onset endotherms at about 133.95, 136.29, 137.54, and 137.96° C., respectively. On average, the DSC thermogram (FIG. 3.2) of the four samples is characterized by a predominant endotherm peak at about 145.52° C. with an onset endotherm at about 136.44° C.

In another aspect of the present invention, crystal Form A also exhibits a DSC thermogram (FIG. 3.2) with an onset of the endotherms at about 133.95, 136.29, 137.54, and 137.96° C., respectively. On average, the DSC thermogram of the four samples is characterized by a predominant endotherm peak at about 145.52° C. with an onset endotherm at about 136.44° C.

In another aspect of the present invention, crystal Form A also exhibits a differential scanning calorimetry thermogram substantially as shown in FIG. 3.1, which is characterized by a predominant endotherm peak at about 145.53° C. or as substantially shown in FIG. 3.2, which displays a range of predominant endotherm peaks at about 144.01 to 146.92° C. and has characteristic PXRD peaks expressed in degrees 2θ (±0.2°) at about one or more of the following positions: 4.70, 9.39, 14.10, 15.70, 17.18, 18.83, 19.12, 20.07, 20.97, 21.42, 22.03, 22.54, 23.62, and 28.42. In another aspect of the present invention, crystal Form A also exhibits a DSC thermogram substantially as shown in FIG. 3.1, which is characterized by a predominant endotherm peak at about 145.53° C. or as substantially shown in FIG. 3.2, which displays a range of predominant endotherm peaks at about 144.01 to 146.92° C. and has characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 4.70, 9.39, 14.10, 15.70, 19.12, 20.97, 22.03, 21.42, 22.54, 23.62, and 28.42. In another aspect of the present invention, crystal Form A also exhibits a DSC thermogram substantially as shown in FIG. 3.1, which is characterized by a predominant endotherm peak at about 145.53° C. or as substantially shown in FIG. 3.2, which displays a range of predominant endotherm peaks at about 144.01 to 146.92° C. and has characteristic PXRD peaks expressed in degrees 2θ (±0.2°) at about the following positions: 17.18, 18.83, 20.07, and further comprising at least one additional diffraction peak expressed in degrees 2θ (±0.2°) selected from the group consisting of peaks at about 21.42 and 28.42. In another aspect of the present invention, crystal Form A also exhibits a DSC thermogram substantially as shown in FIG. 3.1, which is characterized by a predominant endotherm peak at about 145.53° C. or as substantially shown in FIG. 3.2, which displays a range of predominant endotherm peaks at about 144.01 to 146.92° C. and has characteristic PXRD peaks expressed in degrees 2θ (±0.2°) at about the following positions: 17.18, 18.83, 20.07, 21.42, and 28.42. In another aspect of the present invention, crystal Form A also exhibits a DSC thermogram substantially as shown in FIG. 3.1, which is characterized by a predominant endotherm peak at about 145.53° C. or as substantially shown in FIG. 3.2, which displays a range of predominant endotherm peaks at about 144.01 to 146.92° C. and has characteristic PXRD peaks expressed in degrees 2θ (±0.2°) at about the following positions: 17.18, 18.83, 20.07, 21.42, 22.54, and 28.42. In another aspect of the present invention, crystal Form A also exhibits a DSC thermogram substantially as shown in FIG. 3.1, which is characterized by a predominant endotherm peak at about 145.53° C. or as substantially shown in FIG. 3.2, which displays a range of predominant endotherm peaks at about 144.01 to 146.92° C. and has characteristic PXRD peaks expressed in degrees 2θ (±0.2°) at about the following positions: 17.18, 18.83, 20.07, 21.42, 22.54, and 28.42, and further comprising at least one additional diffraction peak expressed in degrees 2θ (±0.2°) selected from the group consisting of peaks at about 4.70, 9.39, 14.10, 15.70, 19.12, 20.97, 22.03, and 23.62.

In another aspect of the present invention, crystal Form A exhibits characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 4.70, 9.39, 14.10, 15.70, 19.12, 20.97, 22.03, 21.42, 22.54, 23.62, and 28.42, and characteristic FT-IR peaks as substantially shown in FIG. 2, and characteristic DSC thermograms as substantially shown in FIG. 3.1 which is characterized by a predominant endotherm peak at about 145.53° C. or as substantially shown in FIG. 3.2, which displays a range of predominant endotherm peaks at about 144.01 to 146.92° C. In another aspect of the present invention, crystal Form A exhibits characteristic PXRD peaks expressed in degrees 2θ (±0.2°) at about the following positions: 17.18, 18.83, and 20.07, and further comprising at least one additional diffraction peak expressed in degrees 2θ (±0.2°) selected from the group consisting of peaks at about 21.42, 22.54, and 28.42, and characteristic FT-IR peaks as substantially shown in FIG. 2, and characteristic DSC thermograms as substantially shown in FIG. 3.1 which is characterized by a predominant endotherm peak at about 145.53° C. or as substantially shown in FIG. 3.2, which displays a range of predominant endotherm peaks at about 144.01 to 146.92° C.

In another aspect of the present invention, crystal Form A exhibits characteristic FT-IR peaks as substantially shown in FIG. 2, and characteristic DSC thermograms as substantially shown in FIG. 3.1 which is characterized by a predominant endotherm peak at about 145.53° C. or as substantially shown in FIG. 3.2, which displays a range of predominant endotherm peaks at about 144.01 to 146.92° C.

In another aspect of the present invention, single crystals of Form A exhibit a basic crystal structure that is monoclinic and has a space group P2(1). The characteristic data of the crystal structure of crystal Form A is shown in Table 3 below.

TABLE 3

Single Crystallographic Data of Crystalline Form A

| Parameter | Form A |
|---|---|
| Class | Monoclinic |
| Space Group | P2(1) |
| a | 10.5041 Å |
| b | 12.9092 Å |
| c | 18.9353 Å |
| α | 90° |
| β | 95.6890° |
| γ | 90° |
| Volume | 2554.97 Å$^3$ |
| Z | 4 |
| Temperature | 273 K |
| Density (calculated) | 1.511 mg/m$^3$ |
| Absorption Coefficient | 3.661 mm$^{-1}$ |
| wavelength | 1.54178 Å | a, b, c = length of unit cell edges
α, β, γ = angles of cell units
Z = number of molecules in the unit cell In another aspect of the present invention is the racemate crystal form of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, designated as the racemate. The racemate is the crystalline state of the racemic mixture of the precipitated approximately equimolar S- and R-enantiomers. The crystal racemate exhibits a PXRD pattern substantially as shown in FIG. 4. The characteristic PXRD peaks of the crystal racemate expressed in degrees 2θ (±0.2° θ), interplanar spacings (d), and respective intensities (%) are displayed in Table 4, below.

TABLE 4

PXRD of the Crystal Racemate (Solid-state racemate)

| Peak | 2-Theta° | d-spacing | Intensity (%) |
|---|---|---|---|
| 1 | 3.40 | 25.98 | 98.1 |
| 2 | 4.47 | 19.75 | 50.8 |
| 3 | 4.74 | 18.64 | 57.8 |
| 4 | 5.23 | 16.87 | 23.8 |
| 5 | 5.50 | 16.05 | 16.4 |
| 6 | 5.95 | 14.84 | 6.3 |
| 7 | 6.11 | 14.45 | 5.4 |
| 8 | 6.32 | 13.97 | 4.9 |
| 9 | 6.57 | 13.44 | 4.1 |
| 10 | 6.92 | 12.76 | 8.6 |
| 11 | 7.28 | 12.14 | 5.2 |
| 12 | 7.87 | 11.22 | 6.5 |
| 13 | 8.19 | 10.78 | 7.5 |
| 14 | 8.44 | 10.47 | 6.4 |
| 15 | 8.99 | 9.83 | 8.8 |
| 16 | 9.45 | 9.35 | 23 |
| 17 | 10.09 | 8.76 | 10.2 |
| 18 | 10.69 | 8.27 | 13.5 |
| 19 | 10.93 | 8.09 | 16.2 |
| 20 | 11.50 | 7.69 | 20.9 |
| 21 | 14.19 | 6.24 | 20.9 |
| 22 | 16.41 | 5.40 | 18.5 |
| 23 | 17.03 | 5.20 | 27.9 |
| 24 | 18.23 | 4.86 | 17.5 |
| 25 | 18.94 | 4.68 | 75.9 |
| 26 | 19.77 | 4.49 | 33.7 |
| 27 | 20.18 | 4.40 | 100 |
| 28 | 21.17 | 4.19 | 23.6 |
| 29 | 22.63 | 3.93 | 30.4 |
| 30 | 23.45 | 3.79 | 22 |
| 31 | 24.18 | 3.68 | 25 |
| 32 | 24.70 | 3.60 | 19.7 |

TABLE 4-continued

PXRD of the Crystal Racemate (Solid-state racemate)

| Peak | 2-Theta° | d-spacing | Intensity (%) |
|---|---|---|---|
| 33 | 25.42 | 3.50 | 17.2 |
| 34 | 26.99 | 3.30 | 17.8 |
| 35 | 27.51 | 3.24 | 21 |
| 36 | 28.04 | 3.18 | 23 |
| 37 | 28.56 | 3.12 | 19.6 |
| 38 | 29.12 | 3.06 | 21.1 |
| 39 | 29.89 | 2.99 | 16.3 |
| 40 | 31.16 | 2.87 | 15.3 |
| 41 | 31.80 | 2.81 | 17 |
| 42 | 33.06 | 2.71 | 15.1 |
| 43 | 33.55 | 2.67 | 16.1 |
| 44 | 35.96 | 2.50 | 15 |
| 45 | 36.63 | 2.45 | 15.1 |
| 46 | 38.67 | 2.33 | 15.9 |
| 47 | 42.57 | 2.12 | 13.7 |
| 48 | 45.72 | 1.98 | 13.7 |

In yet another aspect of the present invention, the crystal racemate has characteristic PXRD peaks expressed in degrees 2θ (±0.2° θ) at one or more of the following positions: 3.4, 4.47, 4.74, 5.23, 17.03, 18.94, 19.77, 20.18, 21.17, 22.63, and 24.18.

In yet another aspect of the present invention, the crystal racemate has characteristic PXRD peaks expressed in degrees 2θ (±0.2° θ) at about one or more of the following positions: 3.4, 4.47, 4.74, 18.94, 19.77, 20.18, and 22.63, all of which have a relative intensity of at least 30%. In yet another aspect of the present invention, the crystal racemate has characteristic PXRD peaks expressed in degrees 2θ (±0.2° θ) at about one or more of the following positions: 3.40, 4.47, 4.74, 18.94, and 20.18, all of which have a relative intensity of at least 50%. In yet another aspect of the present invention, the crystal racemate has characteristic PXRD peaks expressed in degrees 2θ (±0.2° θ) at about one or more of the following positions: 3.40, 18.94, and 20.18, all of which have a relative intensity of at least 75%. In another aspect of the present invention, the crystal racemate has characteristic PXRD peaks expressed in degrees 2θ (±0.2° θ) at about one or more of the following positions: 3.40, 18.94, and 20.18, and further comprising at least one additional diffraction peak expressed in degrees 2θ (±0.2° θ) selected from the group consisting of peaks at about 4.47 and 4.74. In another aspect of the present invention, the crystal racemate has characteristic PXRD peaks expressed in degrees 2θ (±0.2° θ) at about one or more of the following positions: 3.40, 18.94, and 20.18, and further comprising at least one additional diffraction peak expressed in degrees 2θ (±0.2° θ) selected from the group consisting of peaks at about 4.47, 4.74, 19.77, and 22.63. In another aspect of the present invention, the crystal racemate has characteristic PXRD peaks expressed in degrees 2θ (±0.2° θ) at about one or more of the following positions: 3.40, 18.94, and 20.18, and further comprising at least one additional diffraction peak expressed in degrees 2θ (±0.2° θ) selected from the group consisting of peaks at about 4.47, 4.74, 5.23, 17.03, 19.77, 21.17, 22.63, and 24.18.

In another aspect of the present invention, the crystal racemate also exhibits a FT-IR spectrum at the 1800 to 600 cm$^{-1}$ range substantially as shown in FIG. 5. Characteristic FT-IR peaks of the crystal racemate are shown in Table 5 below.

TABLE 5

FT-IR of the Crystal Racemate (Solid-state racemate)

| Peak (cm$^{-1}$) | Absolute Intensity | Relative Intensity | Width |
|---|---|---|---|
| 1662 | −0.397 | 0.483 | 15.67 |
| 1465 | −0.176 | 0.247 | 19.38 |
| 1352 | −0.035 | 0.091 | 10.99 |
| 1301 | −0.394 | 0.457 | 11.14 |
| 1190 | −0.260 | 0.088 | 331.28 |
| 1175 | −0.396 | 0.478 | 29.38 |
| 1132 | −0.224 | 0.231 | 9.00 |
| 1024 | −0.121 | 0.191 | 13.96 |
| 983 | −0.027 | 0.086 | 8.76 |
| 912 | −0.141 | 0.207 | 21.33 |
| 811 | −0.159 | 0.238 | 32.64 |
| 757 | −0.042 | 0.115 | 10.65 |
| 722 | 0.005 | 0.065 | 14.61 |
| 686 | 0.020 | 0.060 | 8.76 |
| 658 | −0.037 | 0.122 | 10.18 |

In another aspect of the present invention, the crystal racemate exhibits characteristic FT-IR peaks at the 1800 to 600 cm$^{-1}$ spectrum range at one or more of the following: 1662, 1465, 1352, 1301, 1190, 1175, 1132, 1024, 983, 912, 811, 757, 722, 686, and 658 cm$^{-1}$.

In another aspect of the present invention, the crystal racemate also exhibits a DSC thermogram substantially as shown in FIG. 6, which is characterized by a predominant endotherm peak at about 241.77° C. with an onset endotherm at about 233.63° C.

In another aspect of the present invention, the crystal racemate is characterized by PXRD peaks expressed in degrees 2θ (±0.2° θ) at one or more of the following positions: 3.4, 4.47, 4.74, 5.23, 17.03, 18.94, 19.77, 20.18, 21.17, 22.63, and 24.18; and with characteristic FT-IR peaks at the 1800 to 600 cm$^{-1}$ spectrum range at one or more of the following: 1662, 1465, 1352, 1301, 1190, 1175, 1132, 1024, 983, 912, 811, 757, 722, 686, and 658 cm$^{-1}$; and with a predominant endotherm peak at about 241.77° C. with an onset endotherm at about 233.63° C.

In another aspect of the present invention, the crystal racemate is characterized by PXRD peaks expressed in degrees 2θ (±0.2° θ) at one or more of the following positions: 3.4, 4.47, 4.74, 18.94, 19.77, 20.18, and 22.63; and with characteristic FT-IR peaks at the 1800 to 600 cm$^{-1}$ spectrum range at one or more of the following: 1662, 1465, 1352, 1301, 1190, 1175, 1132, 1024, 983, 912, 811, 757, 722, 686, and 658 cm$^{-1}$; and with a predominant endotherm peak at about 241.77° C. with an onset endotherm at about 233.63° C.

In another aspect of the present invention, the crystal racemate is characterized by PXRD peaks expressed in degrees 2θ (±0.2° θ) at one or more of the following positions: 3.40, 4.47, 4.74, 18.94, and 20.18; and with characteristic FT-IR peaks at the 1800 to 600 cm$^{-1}$ spectrum range at one or more of the following: 1662, 1465, 1352, 1301, 1190, 1175, 1132, 1024, 983, 912, 811, 757, 722, 686, and 658 cm$^{-1}$; and with a predominant endotherm peak at about 241.77° C. with an onset endotherm at about 233.63° C.

In another aspect of the present invention, the crystal racemate is characterized by PXRD peaks expressed in degrees 2θ (±0.2° θ) at one or more of the following positions: 3.40, 18.94, and 20.18; and with characteristic FT-IR peaks at the 1800 to 600 cm$^{-1}$ spectrum range at one or more of the following: 1662, 1465, 1352, 1301, 1190, 1175, 1132, 1024, 983, 912, 811, 757, 722, 686, and 658 cm$^{-1}$; and with a predominant endotherm peak at about 241.77° C. with an onset endotherm at about 233.63° C.

In another aspect of the present invention is a composition comprising a therapeutically effective amount of crystalline Form A and a pharmaceutically or veterinarily acceptable excipient, diluent, carrier, or mixture thereof.

In another aspect of the present invention is a composition comprising a therapeutically effective amount of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, and a pharmaceutically or veterinarily acceptable excipient, diluent, carrier, or mixture thereof.

In yet another aspect of the present invention is a composition comprising a therapeutically effective amount of amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, and a pharmaceutically or veterinarily acceptable excipient, diluent, carrier, or mixture thereof.

In yet another aspect of the present invention is a composition comprising a therapeutically effective amount of crystalline Form A and the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, and a pharmaceutically or veterinarily acceptable excipient, diluent, carrier, or mixture thereof.

In yet another aspect of the present invention is a composition comprising a therapeutically effective amount of crystalline Form A, the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, or the crystalline racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or any mixture thereof, and a pharmaceutically or veterinarily acceptable excipient, diluent, carrier, or mixture thereof.

In yet another aspect of the invention, the composition is a pharmaceutically or veterinarily acceptable composition.

In yet another aspect of the present invention is a method of treating a parasitic infection or infestation in an animal, comprising administering to the animal in need thereof, a therapeutically effective amount of crystalline Form A.

In yet another aspect of the present invention is a method of treating a parasitic infection or infestation in an animal, comprising administering to the animal in need thereof, a therapeutically effective amount of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)-ethanone, prepared from crystalline Form A.

In yet another aspect of the present invention is a method of treating a parasitic infection or infestation in an animal, comprising administering to the animal in need thereof, a therapeutically effective amount of amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A.

In yet another aspect of the present invention is a method of treating a parasitic infection or infestation in an animal, comprising administering to the animal in need thereof, a therapeutically effective amount of crystalline Form A and the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A.

In yet another aspect of the present invention is a method of treating a parasitic infection or infestation in an animal, comprising administering to the animal in need thereof, a therapeutically effective amount of crystalline Form A, the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, or the crystalline racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or any mixture thereof.

In yet another aspect of the present invention is the use of a medicament comprising a therapeutically effective amount of a compound of crystalline Form A, the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, or the racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or any mixture thereof, for the treatment of a parasitic infection or infestation in an animal in need thereof.

In yet another aspect of the present invention is a pharmaceutical or veterinary composition comprising a therapeutically effective amount of crystalline Form A in combination with at least one additional veterinary agent, and at least one pharmaceutically or veterinarily acceptable excipient, carrier, diluent, or mixture thereof.

In yet another aspect of the present invention is a pharmaceutical or veterinary composition comprising a therapeutically effective amount (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, in combination with at least one additional veterinary agent, and at least one pharmaceutically or veterinarily acceptable excipient, carrier, diluent, or mixture thereof.

In yet another aspect of the present invention is a pharmaceutical or veterinary composition comprising a therapeutically effective amount of the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, in combination with at least one additional veterinary agent, and at least one pharmaceutically or veterinarily acceptable excipient, carrier, diluent, or mixture thereof.

In yet another aspect of the present invention is a pharmaceutical or veterinary composition comprising a therapeutically effective amount of crystalline Form A and the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, in combination with at least one additional veterinary agent, and at least one pharmaceutically or veterinarily acceptable excipient, carrier, diluent, or mixture thereof.

In yet another aspect of the present invention is a pharmaceutical or veterinary composition comprising a therapeutically effective amount of crystalline Form A, the amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, or the racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or any mixture thereof, in combination with at least one additional veterinary agent, and at least one pharmaceutically or veterinarily acceptable excipient, carrier, diluent, or mixture thereof.

In yet another aspect of the present invention, the additional veterinary agent is selected from the group consisting of abamectin, selamectin, moxidectin, ivermectin, emamectin, doramectin, eprinomectin, pyrantel, amitraz, albendazole, cambendazole, fenbendazole, flubendazole, mebendazole, febantel, octadepsipeptides, oxfendazole, oxibendazole, paraherquamide, parbendazole, praziquantel, thiabendazole, tetramisole, triclabendazole, levamisole, oxantel, novaluron, morantel, milbemycin, milbemycin oxime, demiditraz, diethylcarbamazine, fipronil, hydroprene, kinoprene, methoprene, metaflumizone, niclosamide, permethrin, pyrethrins, pyriproxyfen, spinosad, aminoacetonitrile derivative(s), or any mixture thereof.

In yet another aspect of the present invention, the additional veterinary agent is selected from moxidectin or pyrantel, or mixture thereof. In yet another aspect of the present invention, the additional veterinary agent is selected from selamectin. In yet another aspect of the present invention, the additional veterinary agent is selected from moxidectin, pyrantel, and praziquantel, or any mixture thereof. In yet another aspect of the present invention, the additional veterinary agent is selected from pyrantel and milbemycin oxime, or mixture thereof. In yet another aspect of the present invention, the additional veterinary agent is an aminoacetonitrile derivative.

In yet another aspect of the invention, the animal is a companion animal, livestock, or bird. In yet another aspect of the present invention, the companion animal is horse, dog, or cat. In yet another aspect of the present invention, livestock is cattle, swine, or sheep.

In yet another aspect of the present invention, the composition is administered orally, topically, or by injection. In yet another aspect of the present invention, the composition is administered orally. In yet another aspect of the present invention, the composition is administered topically. In yet another aspect of the present invention, the composition is administered by injection. In yet another aspect of the invention, the injection is by subcutaneous, intramuscular, or intravenous administration.

In yet another aspect of the present invention, Form A can be prepared by crystallizing 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone from a solvent comprising ethanol, n-heptane or mixed isomers of hepatanes, n-butanol, ethyl or isopropyl acetate, or any mixture thereof. Further, Form A can be prepared by vapor diffusion between methanol and diisopropyl ether. In yet another aspect of the present invention is a process for the preparation of crystalline Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone. Form A was prepared by adding amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone to a reaction vessel containing ethyl acetate (5%), n-heptane (35%), and ethanol (60%). The reaction mixture was heated to about 60° C. and then cooled to about 45° C. over a period of about 15-20 minutes. Crystal Form A seeds can then be added to the mixture. [The seeds were made by dissolving amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone in methanol and allowing vapor diffusion of an outer layer of diisopropyl ether to slowly convert the amorphous form to Form A over a period of about 5 days at room temperature.] Maintain the reaction mixture at about 45° C. for about 2-hours then cool to about 30° C. at a rate of about 1.5° C. per hour, then cool to 10° C. over three hours, linearly, then hold at 10° C. for about 4.5 hours. Cool the white slurry to about 0-1° C. over 20 minutes and hold overnight (approximately 23 hours) at about 0-1° C. Alternatively, the reaction mixture can be cooled to about 20° C. over 12.5 hours (about 2° C./hr) linearly, then held at 20° C. while adding n-heptane over 1 hour. Hold the mixture at 20° C. for about 1-hour and then cool, and subsequently cool to −10° C. over 10 hours and hold at −10° C. for 3 hours. Add the mixture to a pre-chilled sintered glass filter and filter under vacuum. Rinse the remaining solids with a mixture of a solvent mixture containing about 40/60 to about 20/80 ethanol/n-heptane. The solvent mixture can be pre-chilled to about 0° C. The remaining solids can be washed again with n-heptane. The ethanol used in the procedure described herein was denatured with 0.5% toluene. The solids can then be dried under vacuum for about 1 hour at room temperature and then under vacuum at 40° C. overnight. Alternatively, the solids can be dried in a vacuum oven at 30° C. over a period of 2.5 days, at a pressure of about 150-160 torr with a nitrogen sweep. The resulting solids are crystalline Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone as confirmed by DSC.

BRIEF DESCRIPTION OF THE DRAWINGS

FIG. 1. Depicts an illustrative PXRD pattern of crystalline Form A.

FIG. 2. Depicts an illustrative FT-IR spectrum of crystalline Form A.

FIG. 3.1. Depicts an illustrative DSC thermogram of a single lot of crystalline Form A.

FIG. 3.2. Depicts an illustrative DSC thermogram of 4-lots of crystalline Form A.

FIG. 4. Depicts an illustrative PXRD pattern of the crystal racemate.

FIG. 5. Depicts an illustrative FT-IR spectrum of the crystal racemate.

FIG. 6. Depicts an illustrative DSC thermogram of the crystal racemate.

DETAILED DESCRIPTION

The person skilled in the art of crystallizing solid state forms of pharmaceutical or veterinary active compound(s)/ agent(s) will understand that the general approach involves finding conditions under which the desired active pharmaceutical/veterinary agent is soluble, and other conditions in which the same compound is not soluble, and modifying the conditions such that the solubility decreases and the crystals grow. Methods include changing temperature, addition of an anti-solvent, addition of a concentrated solution of the compound to an anti-solvent, modification of pH, distillation of solvent, or some combination thereof. Seeds may be added to encourage crystallization. General methods can be found from the prevalent literature, such as *Crystallization*, 4$^{th}$ Ed, J. W. Mullin, Butterworth-Heinemann, 2001, or *Crystallization of Organic Compounds: An Industrial Perspective*, by H.-H. Tung et al., 2009, Wiley-AIChE. As such, a person skilled in the art may uncover a variety of processes by which crystalline Form A and the crystal racemate may be obtained, including other potential crystalline forms.

The solid-state form of a compound can materially affect the physical properties of the compound including: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; or (6) filtration properties. Selection and control of the solid-state form is particularly important for compounds that are to be used as a pharmaceutical or veterinary agent. Careful selection and control of the solid-state form can reduce synthesis, processing, formulation, and/or administration problems associated with the compound.

Crystallization of the Formula (1) compound is expected with a number of appropriate solvents and anti-solvents, and mixtures thereof, either by cooling by addition of an anti-solvent or by distillation of a solvent. Non-limiting examples of solvents include: methanol, ethanol, other alcohols, acetone, methyl ethyl ketone, methyl isobutyl ketone, other ketones, ethyl acetate, propyl acetate, butyl acetate, other acetates, toluene, acetonitrile, tetrahydrofuran, 2-methyl tetrahydrofuran, acetic acid, dichloromethane, 1,2-dichloroethane, 2,2,2-trichloroethanol, other chlorinated organic solvents, and the like. Non-limiting examples of antisolvents include: water, heptane, hexane, octane, t-amyl alcohol, cyclohexane, t-butyl methyl ether, diisopropyl ether, ethyl ether, other ethers and other alkanes.

It has been found that the specific crystal form, Form A, of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone according to the present invention exhibits advantages during processing in organic materials in comparison to the crystal racemate or the individual amorphous enantiomers of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone.

The solubility of the crystal racemate is less than 10 mg/mL in acetone at room temperature (i.e., approximately 22° C. In contrast, the solubility of crystalline Form A is greater than 300 mg/mL in acetone. Further, the solubility of the crystal racemate and Form A in methyl t-butyl ether is <1 mg/mL and 11 mg/mL, respectively. This difference in solubility is typical of other solvents as well.

This vast difference in solubility has a few advantages. First, separation of the racemate from the enantiopure S-enantiomer is performed by filtration of the racemate from solution. The enantiomeric purity is thus upgraded from approximately 80% enantiomeric excess (90:10) to approximately 98% enantiomeric excess (99:1). Secondly, the higher solubility of the S-enantiomer allows for solutions of much greater concentration for any liquid formulation work. For instance, making a spray dried dispersion of the S-enantiomer requires dissolution of the crystalline Form A. The higher the solubility, the less processing time required, and the less solvent required. Thirdly, since Form A is much more soluble than the crystal racemate, this may correlate with greater bioavailability.

Another key difference between the crystal racemate and crystal Form A is the particle size. The crystal racemate produces very small primary particles, generally less than 1 micron, which are agglomerated. These particles are very difficult to filter, owing to the small primary particle size. A filter aid such as celite is frequently used to perform the filtration of the crystal racemate. Crystal Form A crystallizes as larger particles, exhibiting primary particles in excess of 10 microns, even in excess of 100 microns on the longest axis. No filter aid or special equipment such as a centrifuge is required to filter those particles from suspensions in, for example, ethanol/heptane mixtures or n-butanol. The use of filter aid to isolate the final Form A would present large challenges around removing the filter aid from the active ingredient (i.e., Form A). While particle size is a function of how rapidly the crystals form, the solvent system employed, seeding, and other factors, the vast difference in particle size between the crystal racemate and crystal Form A has persisted through numerous crystallizations.

In contrast to the amorphous state isolated by evaporation of the solvent resulting in a foamy solid, crystal Form A is a flowable powder. Crystal Form A also has a higher melting point than the amorphous state, which melts at 112-124° C. as viewed by hot stage microscopy and therefore easier to dry of residual solvents.

ABBREVIATIONS AND DEFINITIONS

The abbreviation "DSC" refers to differential scanning calorimetry.

The abbreviation "PXRD" or "pxrd" refers to powder X-ray diffraction, which can also be referred to as X-ray powder diffraction (XRPD).

The abbreviation "FT-IR" refers to Fourier-transform infrared spectroscopy.

"Additional veterinary agent(s)" as used herein, unless otherwise indicated, refers to other veterinary or pharmaceutical compounds or products that provide a therapeutically effective (pharmacologically and/or antiparasitically active) amount of said agent(s) that are useful for the treatment or control of a parasitic infection or infestation in an animal, as described herein.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Chiral", as used herein, unless otherwise indicated, refers to the structural characteristic of a molecule that makes it impossible to superimpose it on its mirror image, (e.g., R- and S-enantiomers). The term is also depicted as an asterisk (i.e., *) in some of the Examples and preparations.

"Compound(s) of the present invention", as used herein, unless otherwise indicated, refers to the crystalline forms 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, herein crystal Form A and the crystal racemate. The phrase also refers to the amorphous S-enantiomeric form of the compound that is subsequently prepared from crystal Form A, for example, when present in a solid formulation as a result of a spray dry dispersion application.

"Crystalline form", as used herein, unless otherwise indicated, refers to specific solid state forms of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, wherein the molecules are arranged to form a distinguishable crystal lattice (i) comprising distinguishable unit cells and (ii) yielding distinguishable diffraction peaks when subjected to X-ray radiation.

"Form A", as used herein, unless otherwise indicated, refers to the specific crystal solid state form of the (S)-enantiomer of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, wherein the molecules are arranged to form a distinguishable crystal lattice (i) comprising distinguishable unit cells and (ii) yielding distinguishable diffraction peaks when subjected to X-ray radiation.

"Crystal racemate" or "crystalline racemate" as used herein, unless otherwise indicated, refers to the specific crystal solid state form of the (S/R)-racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, wherein the molecules are arranged to form a distinguishable crystal lattice (i) comprising distinguishable unit cells and (ii) yielding distinguishing diffraction peaks when subjected to X-ray radiation.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids and insects) which feed through or upon the skin of its host. Preferred arachnids are of the order Acarina, e.g., ticks and mites. Preferred insects are midges, fleas, mosquitoes, biting flies (stable fly, horn fly, blow fly, horse fly, and the like), bed bugs, and lice. The compounds of the present invention can be used for the treatment of parasites, i.e., treatment of a parasitic infection or infestation.

"Therapeutically effective amount", as used herein, unless otherwise indicated, refers to an amount of a compound of the present invention alone or in combination with at least one other additional veterinary agent, that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary (or pharmaceutically) acceptable" as used herein, unless otherwise indicated, indicates that the substance (e.g., excipient, carrier, diluent, or mixture thereof) must be compatible chemically and/or toxicologically, with the other ingredients comprising a formulation, composition, and/or the animal being treated therewith, and is not deleterious to the animal. For the purpose of excipient, carrier, diluents, the terms refer to any acceptable ingredient other than the compound of the present invention or any additional veterinary agent used to formulate a final dosage form, for example, a tablet, topical solution or suspension, or injectable solution.

Characterization of Crystalline Forms

The crystalline state of a compound can be described by several crystallographic parameters, including single crystal structure, powder X-ray diffraction pattern (PXRD), Fournier-transform infrared (FT-IR) absorption spectroscopy pattern, and differential scanning calorimetry (DSC).

Single Crystal X-Ray Analysis

The crystal structure of a single crystal of Form A was determined by single crystal X-ray diffraction analysis. Data collection was performed on a Bruker APEX diffractometer at room temperature. The structure was solved by direct methods using SHELX software suite in the space group P2(1). The structure was subsequently refined by the full-matrix least squares method. All non-hydrogen atoms were found and refined using anisotropic displacement parameters. The hydrogen atoms located on nitrogen and oxygen were found from the Fourier difference map and refined freely. The remaining hydrogen atoms were placed in calculated positions and were allowed to ride on their carrier atoms. The final refinement included isotropic displacement parameters for all hydrogen atoms. Analysis of absolute configuration was performed by examination of the flack parameter. In this case, the parameter=0.002 with an estimated standard deviation of 0.0018; within range for absolute configuration determination. The final R-index was 3.7%. A final difference Fourier revealed no missing or misplaced electron density.

Instrument and Method Fournier Transform-Infrared Spectroscopy (FT-IR)

The FT-IR spectrum of crystal Form A and crystal racemate, as described herein, were acquired using a Bruker FT-IR Vertex 70 spectrometer equipped with a Pike Technologies MIRacle ATR single reflection ATR accessory (Germanium Single Reflectance Plate). The spectra were collected at 4 cm$^{-1}$ resolution with a co-addition of 16 scans. Because the FT-IR spectra were recorded using single reflection ATR, no sample preparation was required. Using ATR FT-IR will cause the relative intensities of infrared bands to differ from those seen in a transmission FT-IR spectrum using KBr disc or nujol mull sample preparations. Due to the nature of ATR FT-IR, the bands at lower wave number are more intense than those at higher wavenumber. Spectra were subtracted from a blank run and atmospheric compensation and vector normalization was performed.

Instrument and Method Powder X-Ray Diffraction (PXRD)

The crystal structures of crystal Form A and crystal racemate, as described herein, were analyzed using powder X-ray diffraction (PXRD). The X-ray diffractograms were obtained using a Bruker AXS [Coventry, UK] Endeavor D4 equipped with a LynxEye detector operated with a fixed slit and a Cu source operated at 40 kV and 40 mA, K2a wavelength 1.5406 angstroms. The diffractogram was obtained in the region of 3 to 50 degrees two-theta. The step size was 0.020 degrees two-theta, and the acquisition time per step was 0.5 seconds. During acquisition, the sample holder was rotated at 20 rpm. Samples were prepared for analysis by spreading loose solids on zero-background silica wafers in such a fashion as to provide a level surface for the analysis. Data were analyzed in the EVA software package obtained from Bruker AXS.

As will be appreciated by the skilled crystallographer, the relative intensities of the various peaks reported in the Tables and Figures herein may vary due to a number of factors such as orientation effects of crystals in the X-ray beam or the purity of the material being analyzed or the degree of crystallinity of the sample. The PXRD peak positions may also shift for variations in sample height but the peak positions will remain substantially as defined in Tables 1 and 4, for crystal Form A and crystal racemate, respectively.

The skilled crystallographer also will appreciate that measurements using a different wavelength will result in different shifts according to the Bragg equation–nA, =2ci sin Θ. Such further PXRD patterns generated by use of alternative wavelengths are considered to be alternative representations of the PXRD patterns of the crystalline materials of the present invention and as such are within the scope of the present invention.

Instrument and Method Differential Scanning Calorimetry (DSC)

Analysis was performed on a Mettler Toledo DSC 823e in a 40 µL aluminum pan, with matching reference pan. The sample was heated at 10° C. per minute from 25° C. to a sufficiently high temperature to achieve melting of the sample. Evaluation of the data was completed in the StarE software package, version 11.

General Scheme-Preparation

In the scheme, preparations, and examples below, the following catalysts/reactants and miscellaneous abbreviations include: mobile phase (MP); N,N-dimethyl formamide (DMF); ethanol (EtOH); methyl tert-butyl ether (MTBE); methanol (MeOH), tetrahydrofuran (THF); ethyl acetate (EtOAc); trifluoroacetic acid (TFA); 1,3-bis(diphenylphosphino)propane (DPPP); amidecarbonyldiimidazole (CDI); isopropylmagnesium chloride-lithium chloride (iPrMgCl—LiCl); t-butyloxycarbonyl (BOC); palladium(II) acetate (Pd(OAc)$_2$); lithium borohydride (LiBH$_4$); tert-butyl methyl ether (TBME); and 1,2-dichloroethane (DCE).

The Formula (1) compound, 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, can be prepared in accordance with preparations and procedures as described in WO2012/120399. An alternate, yet similar preparatory scheme is shown below.

Step 1: Chalcone preparation
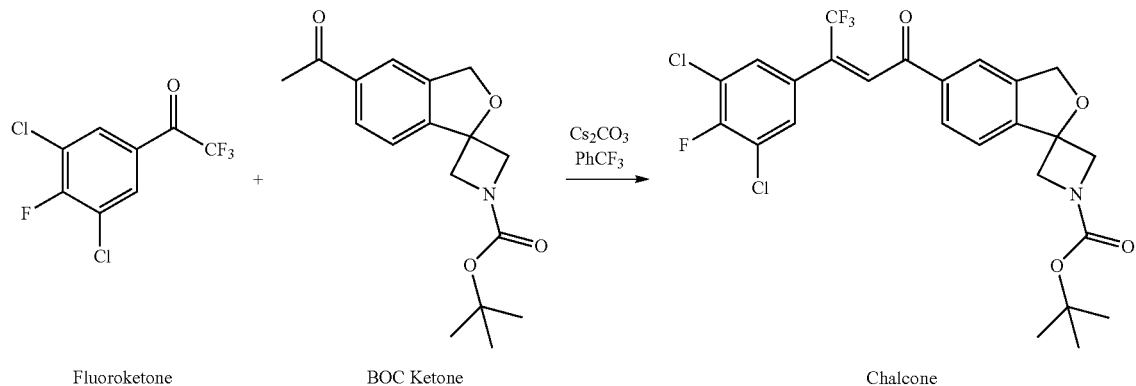
Step 2: Asymmetric isoxazoline synthesis
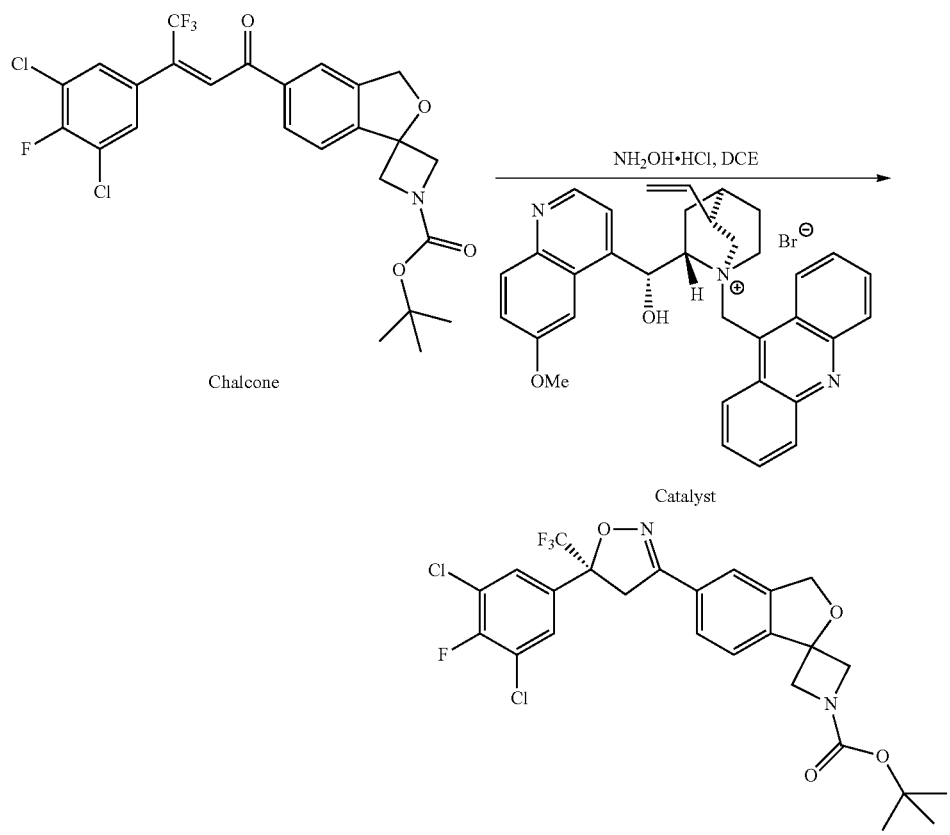
Step 3: BOC deprotection
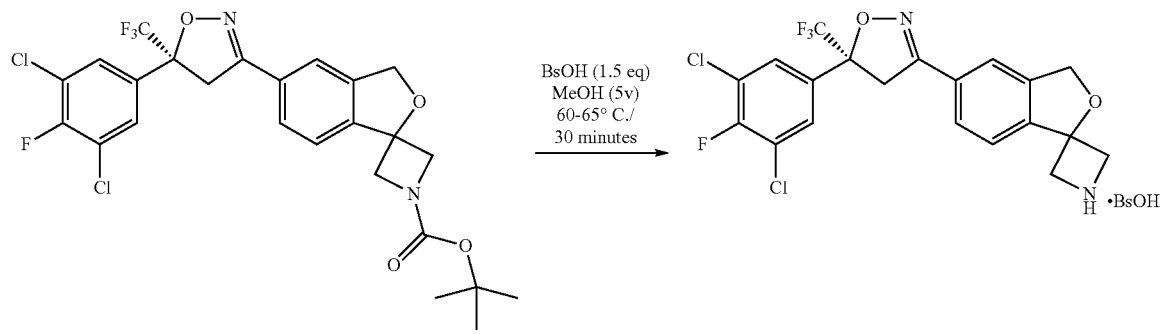

step 4: Amide coupling

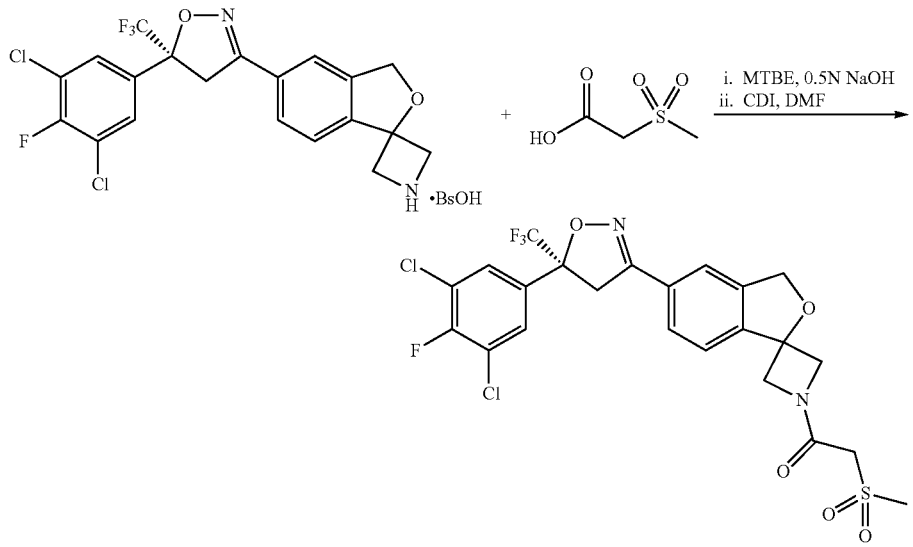

Synthesis of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone. The chalcone is achiral. The chiral phase-transfer catalyst is used to close the 5-membered ring in a fashion that gives about 90% S-enantiomer and about 10% R-enantiomer. The deprotection of the boc group (tert-butoxycarbonyl) occurs in the presence of benzene sulfonic acid and methanol, wherein the chiral purity is maintained. The neutralized amine is then coupled with 2-(methylsulfonic)acetic acid providing the desired compound which is still about 90% S-enantiomer and about 10% R-enantiomer. The racemate crystallizes out, e.g., equimolar amounts of the S- and R-enantiomer which is filtered off with the aid of a filter aid, (Celite) thus leaving the enantiomerically pure S-enantiomer as an amorphous solid.

Pharmaceutical/Veterinary Compositions

The compound of the present invention can be administered alone or in a formulation appropriate to the specific use envisaged, the particular species of host animal being treated and the parasite involved. Generally, it will be administered as a formulation in association with one or more pharmaceutically or veterinarily acceptable excipients, diluents, carriers, or mixtures thereof. The term "excipient", "diluent" or "carrier" is used herein to describe any ingredient other than the compound of the present invention or any additional veterinary (e.g., antiparasitic) agent. The choice of excipient, diluent, or carrier will to a large extent depend on factors such as the particular mode of administration, the effect of the excipient, carrier, diluent, or mixture thereof, on solubility and stability, and the nature of the dosage form. In addition to the excipients, the amount of the compound of the present invention that is administered and the dosage regimen for treating a condition or disorder with the compound depends on a variety of factors, including the age, weight, sex and medical condition of the animal, the severity of the disease, the route and frequency of administration, and thus may vary widely.

In one aspect, the pharmaceutical composition comprises Form A and a pharmaceutically or veterinarily acceptable excipient, carrier, diluent, or mixture thereof. In another aspect, the pharmaceutical composition comprises the amorphous form of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl) ethanone prepared from crystal Form A, and a pharmaceutically acceptable excipient, carrier, diluent, or mixture thereof. The concentration range will vary depending on the composition (e.g., oral, topical, or injectable). Oral dose ranges of the active (i.e., Formula (1) compound) is about 0.1 to 50 mg/kg, preferably from about 0.5 to 25 mg/kg, and even more preferably from about 0.5 to 10 mg/kg, and most preferably from about 1 to 5 mg/kg. For dosing, a 1 mg/kg, 2 mg/kg, 3 mg/kg, 4 mg/kg, and 5 mg/kg regimen is contemplated, including fractional amounts. For a topical solution, the range of active is about 0.1 to 1000 mg/mL, and preferably from about 0.5 to 500 mg/mL, and more preferably from about 1 to 250 mg/mL, and even more preferably from about 2 to 200 mg/mL. The anticipated topical dose will range from about 1 to 50 mg/kg with a preferred dose of about 2 to 40 mg/kg, and more preferred of about 5 to 30 mg/kg, with an even more preferred dose of about 10 to 25 mg/kg. Depending upon the final volumes of the topical solution(s), the concentration of the active can change from that described above. Generally, injectable doses tend to be, but not always, lower in concentration.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation can be prepared by mixing Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone with a pharmaceutically or veterinarily acceptable excipient, carrier, diluent, or mixture thereof. A typical formulation can also be prepared by mixing the amorphous S-enantiomer of the compound prepared from crystal Form A with a pharmaceutically or veterinarily acceptable excipient, carrier, diluent, or mixture thereof. Suitable excipients, carriers, and diluents are well known to those skilled in the art and include materials such as carbohydrates, waxes, water soluble and/or swellable polymers, hydrophilic or hydrophobic materials, gelatin, oils, solvents, water, and the like. The particular excipient, carrier, diluent, mixture thereof, will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary product (i.e., medicament). The compound of the present invention will typically be formulated into veterinary dosage forms to provide an easily controllable dosage form for administration.

Additionally, crystal Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone or the amorphous S-enantiomer of the compound prepared from crystal Form A can be used in spray dry dispersions to form solid amorphous dispersions. The compound of the invention can exist within the solid amorphous dispersion as a pure phase, as a solid solution of drug homogeneously distributed throughout the polymer or any combination of these states or those states that lie intermediate between them. The dispersion is preferably substantially homogeneous so that the amorphous drug is dispersed as homogeneously as possible throughout the polymer. As used herein, "substantially homogeneous" means that the fraction of drug that is present in relatively pure amorphous domains within the solid dispersion is relatively small, on the order of less than 20%, and preferably less than 10% of the total amount of drug. By "amorphous" is meant simply that the drug in the dispersion is in a non-crystalline state. This solid amorphous dispersion can then be used to formulate the compound of the present invention with other pharmaceutically or veterinarily acceptable excipients, carriers, diluents, or mixtures thereof.

The methods by which the compound of the present invention may be administered include oral, topical, and injectable (e.g., parenteral and subcutaneous) administration.

The compound of the present invention can be administered orally by capsule, bolus, tablet, powders, lozenges, chews, multi and nanoparticulates, gels, solid solution, films, sprays, or liquid form. This is a preferred method of administration and as such it is desirable to develop the compound for oral administration. Such formulations may be employed as fillers in soft or hard capsules, soft or hard palatable chews, which typically comprise a carrier, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the compound of the present invention in a suitable medium (e.g., triethylene glycol, benzyl alcohol, and the like). The compound of the present invention can also be formulated with a food substance, e.g., a dietary admixture (food pellets or powder for birds).

The compound of the present invention can be administered topically to the skin or mucosa, that is dermally or transdermally. This is another preferred method of administration and as such it is desirable to develop the compound of the present invention to be suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm. Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the compound of the present invention has increased persistence of action and is more durable, for example it may be more water-fast.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinarily acceptable amount of a compound of the present invention alone, or with a veterinarily acceptable excipient, diluent, or carrier, and optionally an additional veterinary agent, or veterinarily acceptable salt thereof. Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal. The volume of the applied composition can be from about 0.2 mL/kg to 5 mL/kg and preferably from about 1 mL/kg to 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

Injectable (e.g., subcutaneous and parenteral) formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with an additional veterinary agent in the liquid carrier such that the final formulation contains from about 0.01 to 30% by weight of the active ingredients.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilisation, may readily be accomplished using standard veterinary techniques well known to those skilled in the art. The solubility of a compound of the present invention used in the preparation of an injectable solution may be increased by the use of appropriate formulation techniques, such as the incorporation of solubility-enhancing agents.

Administration of the compound of the instant invention is contemplated to be once a month. However, an extended duration formulation may allow for dosing once every 2, 3, 4, 5, or 6 months. A once a year dose is also contemplated.

Method of Use

The present invention further comprises methods for treating a parasitic infection or parasitic infestation in an animal having or being susceptible to such infection or infestation, by administering to the animal in need thereof, a therapeutically effective amount of a compound of the present invention.

The compound, 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone is useful as an antiparasitic agent, therefore, another aspect of the present invention is the use of a pharmaceutical or veterinary composition comprising a therapeutically effective amount of Form A or the amorphous S-enantiomer prepared from crystal Form A, and optionally, a pharmaceutically or veterinarily acceptable excipient, diluent, carrier, or mixture thereof for the treatment of a parasitic infection or infestation in an animal. Similarly, Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone or the amorphous S-enantiomer of the compound prepared from crystal Form A can be used in the manufacture of an antiparasitic medicament for the therapeutic applications described herein.

The compound of the present invention, and compositions comprising a therapeutically effective amount of said compound and a veterinarily acceptable excipient, diluent, carrier, or mixture thereof, are useful as ectoparasiticides for the control and treatment of infections or infestations manifested by said ectoparasite in an animal. The compound of the present invention has utility as an ectoparasiticide, in particular, as an acaricide and insecticide. The compound of the present invention may, in particular, be used in the fields of veterinary medicine, livestock husbandry and the maintenance of public health: against acarids and insects which are parasitic upon vertebrates, particularly warm-blooded vertebrates, including companion animals, livestock, and fowl. Some non-limiting examples of ectoparasites include: ticks (e.g., *Ixodes* spp. (e.g., *I. scapularis, I. ricinus, I. hexagonus*), *Rhipicephalus* spp. (e.g., *R. sanguineus*), *Boophilus* spp., *Amblyomma* spp. (e.g., *A. maculatum, A. triste, A. parvum, A. ovale, A. oblongoguttatum, A. aureolatum, A. cajennense, A. americanum*), *Hyalomma* spp., *Haemaphysalis* spp., *Dermacentor* spp. (e.g., *D. variabilis, D. andersoni, D. marginatus*), *Ornithodorus* spp., and the like); mites (e.g., *Dermanyssus* spp., *Cheyletiella* spp., *Sarcoptes* spp. (e.g., *S. scabiei*), *Psoroptes* spp. (e.g., *P. bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Haematopinus* spp., *Solenoptes* spp., *Trichodectes* spp., *Felicola* spp., and the like); fleas (e.g., *Ctenocephalides* spp., and the like); biting flies, midges, and mosquitoes (e.g., *Tabanus* spp., *Haematobia* spp., *Musca* spp., *Stomoxys* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Dermatobia* spp., *Hypoderma bovis, H. lineatum*).

Compounds of the invention can also be used for the treatment of endoparasites, for example, cestodes (tapeworms), nematodes (round worms), and trematodes (flukes). Non-exlusive examples of the nematodes include roundworms, hookworms, whipworms, and heart worms. Non-exclusive examples of the gastrointestinal roundworms include: *Ostertagia ostertagi* (including inhibited larvae), *O. lyrata, Haemonchus placei, H. similis, H. contortus, Toxascaris leonine, Toxocara canis, T. cati, Trichostrongylus axei, T. colubriformis, T. longispicularis, Cooperia oncophora, C. pectinata, C. punctata, C. surnabada* (syn. *mcmasteri*), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatus, O. columbianum, O. quadrispinulatum, Trichuris* spp., and the like. Non-exclusive examples of hookworm (e.g., *Ancylostoma caninum, A. tubaeforme, A. braziliense, Uncinaria stenocephala*, and the like); lungworm (e.g., *Dictyocaulus viviparus* and *Metastrongylus* spp); eyeworm (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the super-family Filarioidea and the Onchocercidae Family. Non-limiting examples of filarial nematodes within the Onchocercidae Family include the genus *Brugia* spp. (i.e., *B. malayi, B. pahangi, B. timori*, and the like), *Wuchereria* spp. (i.e., *W. bancrofti*, and the like), *Dirofilaria* spp. (i.e., *D. immitis, D. ursi, D. tenuis, D. spectans, D. lutrae*, and the like), *Dipetalonema* spp. (i.e., *D reconditum, D. repens*, and the like), *Onchocerca* spp. (i.e., *O. gibsoni, O. gutturosa, O. volvulus*, and the like), *Elaeophora* spp. (i.e., *E. bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*). Non-exclusive examples of cestodes include: *Taenia saginata, T. solium, T. taeniaformis, Hymenolepsis nana, H. diminuta, Dipylidium caninum; Diphyllobothrium latum; Echinococcus* spp., *Mesocestoides* spp., and *Spirometra* spp. Non-exclusive examples of trematodes include: *Paragonimus kellicotti, Alaria* spp., *Nanophyetus salmincola, Heterobiharzia Americana, Platynosomum fastosum, Schistosoma* spp., and *Fasciola* spp.

The compositions of the invention can be administered in a way appropriate to the specific use envisaged, the particular host animal and weight of host animal being treated, the parasite or parasites involved, degree of infestation, etc., according to standard veterinary practice. The veterinary practitioner, or one skilled in the art, will be able to determine the dosage suitable for the particular animal, which may vary with the species, age, weight, and response. The average doses are exemplary of the average case. Accordingly, higher or lower dosage ranges may be warranted, depending upon the above factors, and are within the scope of this invention.

The compound of the present invention, or a suitable combination of a compound of the present invention and at least one additional veterinary agent, may be directly administered to the animal. The local environment where the animal dwells (e.g., bedding, enclosures, and the like) can also be treated directly or indirectly (e.g., administration to the animal). Direct administration to the animal includes contacting the skin, fur, or feathers of a subject animal with the compound of the present invention, or by feeding (e.g., capsule, tablet, palatable matrix, dietary admixture, and the like) or injection. The compound of the present invention and a composition thereof, including those compositions comprising at least one other biological agent are of value for the treatment and control of the various lifecycle stages of insects and parasites including egg, nymph, larvae, juvenile and adult stages.

The composition of the present invention may be administered alone, as described above, or in combination with at least one other additional antiparasitic agent to form a multi-component parasiticide giving an even broader spectrum of pharmaceutical and/or veterinary utility. Thus, the present invention also envisions a combination veterinary composition comprising an effective amount of the compound of the present invention in combination with at least one other additional antiparasitic agent and can further comprise at least one veterinarily acceptable excipient, diluent, carrier, or mixture thereof.

The following list of additional veterinary agents together with which the compound of the present invention can be used is intended to illustrate the possible combinations, but not to impose any limitation. Non-limiting examples of additional veterinary agents include: amitraz, arylpyrazoles, amino acetonitriles, anthelmintics (e.g., albendazole, cambendazole, dichlorvos, fenbendazole, flubendazole, levamisole, mebendazole, monepantel, morantel, octadepsipeptides, oxantel, oxfendazole, oxibendazole, paraherquamide, parbendazole, piperazines, praziquantel, pyrantel, thiabendazole, tetramisole, triclabendazole, and the like), avermectins and derivatives thereof (e.g., abamectin, doramectin, emamectin, eprinomectin, ivermectin, moxidectin, selamectin, milbemycin, milbemycin oxime, and the like), DEET, demiditraz, diethylcarbamazine, fipronil, insect growth regulators (e.g., lufenuron, novaluron, hydroprene, kinoprene, methoprene, and the like), metaflumizone, niclosamide, nitenpyram, permethrin, pyrethrins, pyriproxyfen, spinosad, and the like. In certain instances, combinations of a compound of the present invention with at least one additional veterinary agent can result in a greater-than-additive effect. Non-limiting examples of combinations include, but are not limited to: compound of the present invention with pyrantel, compound of the present invention with macrocyclic lactone, combination of the present invention with macrocyclic lactone and levamisole, compound of the present invention with macrocyclic lactone and pyrantel.

The veterinary composition for application to an animal may be packaged in a variety of ways depending upon the method used for administering the compound of the present invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

EXAMPLES

Preparation 1: tert-butyl 5'-bromo-3'H-spiro[azetidine-3,1'-isobenzofuran]-1-carboxylate

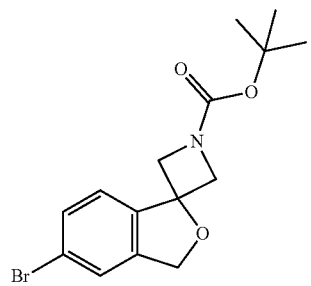 [SMILES: CC(C)(C)OC(=O)N1CC2(C1)OCc1cc(Br)ccc12]

4-bromo-2-(chloromethyl)-1-iodobenzene (500 g, 1.509 moles) was dissolved in tetrahydrofuran (3750 mL) and cooled to −20° C. i-PrMgCl—LiCl (1.3M solution in THF) (1275 ml, 1.66 moles) was added at less than −15° C. The reaction mixture was cooled to −20° C. 3-oxo-azetidine-1-carboxylic acid, tert-butyl ester (310 g, 1.81 moles), as a solution in tetrahydrofuran (750 mL), was added. The reaction was warmed to room temperature over 90 minutes, and then stirred overnight. 1M Aqueous citric acid solution (2 L) was added, followed by tert-butylmethylether (2 L). The mixture was shaken. The organic phase was separated, dried over anhydrous magnesium sulphate, filtered and evaporated to dryness to give an orange oil. The oil was dissolved in ethanol (2.5 L) and the solution diluted with water (1 L). The mixture stood at room temperature, overnight. The resulting crystals of tert-butyl 5'-bromo-3'H-spiro[azetidine-3,1'-isobenzofuran]-1-carboxylate were filtered under reduced pressure and dried under vacuum at 50° C., giving 290 g. $^1$H NMR (CDCl$_3$) δ ppm: 1.49 (9H, s), 4.15 (2H, d), 4.34 (2H, d), 5.11 (2H, s), 7.38 (2H, m), 7.56 (1H, d).

Preparation 2: tert-butyl 5'-acetyl-3'H-spiro[azetidine-3,1'-isobenzofuran]-1-carboxylate

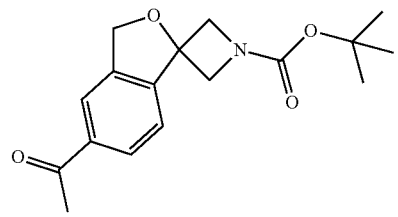 [SMILES: CC(=O)c1ccc2c(c1)COC21CN(C(=O)OC(C)(C)C)C1]

In a scintillation vial containing in 15 mL of ethanol was added Pd(OAc)$_2$ (8.3 mg, 0.037 mmol) and DPPP (31 mg, 0.073 mmol). The reaction vessel was purged with nitrogen gas, capped, and heated to 60° C. for 18 hours. To this was added tert-butyl 5'-bromo-3'H-spiro[azetidine-3,1'-isobenzofuran]-1-carboxylate (Preparation 1, 250 mg, 0.74 mmol) and triethylamine (205 µL, 1.5 mmol) and the mixture was heated to 90° C. for 5 minutes. Butyl vinyl ether (190 uL, 1.5 mmol) was subsequently added and the reaction was heated to 90° C. for 4 hours under nitrogen. The reaction was cooled and 1.0N HCl (2 mL) was added at room temperature and stirred for 2 hours. The reaction was neutralized with saturated NaHCO$_3$ and extracted with EtOAc. The organic phase was dried (Na$_2$SO$_4$) and concentrated under vacuum. The crude material was chromatographed (12 g Redi-Sep column) eluting from 100% hexanes to 35:65 EtOAc:hexanes to afford the intermediate (172 mg, 77%) as a solid. $^1$HNMR (CDCl$_3$) δ ppm: 8.01 (1H), 7.83 (1H), 7.58 (1H), 5.17 (2H) 4.35 (2H), 4.16 (2H), 2.64 (3H), 1.51 (9H); m/z (CI) 204 ([M+H−100]$^+$.

Preparation 3: 1-(4-chloro-3,5-difluorophenyl)-2,2,2-trifluoroethanone

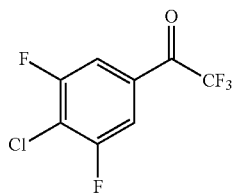 [SMILES: O=C(c1cc(F)c(Cl)c(F)c1)C(F)(F)F]

5-bromo-2-chloro-1,3-difluorobenzene (2000 mg, 8.2 mmol) was stirred at room temperature in THF under N$_2$ and the i-PrMgCl—LiCl (1.3M solution in THF) was added over about 1 minute—very slight exotherm noticed to ~30° C. Reaction was stirred at room temperature for 30 minutes followed by the addition of methyl trifluoroacetate (1580 mg, 12.3 mmol, 1.24 mL) over about 1 minute—slight exotherm to ~40° C. Solvents were evaporated under reduced pressure to provide the desired product. $^1$H NMR (CDCl$_3$) δ ppm: 8.05 (s, 2H).

Preparation 4: tert-butyl 5'-(3-(3,5-dichloro-4-fluorophenyl)-4,4,4-trifluorobut-2-enoyl)-3'H-spiro[azetidine-3,1'-isobenzofuran]-1-carboxylate

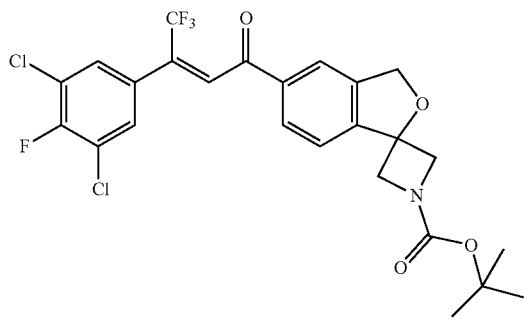 [SMILES: CC(C)(C)OC(=O)N1CC2(C1)OCc1cc(C(=O)/C=C(/c3cc(Cl)c(F)c(Cl)c3)C(F)(F)F)ccc12]

1-(3,5-dichloro-4-fluorophenyl)-2,2,2-trifluoroethanone (Preparation 3, 59.4 g, 227 mmols) and tert-butyl 5'-acetyl-3'H-spiro[azetidine-3,1'-isobenzofuran]-1-carboxylate (Preparation 2, 60.0 g, 198 mmols) were mixed in a 1:1 mix of toluene and trifluoromethylbenzene (250 ml) in a 1 L three necked flask. One neck was equipped with a modified short path Dean-Stark head with a condenser on top, and the other with a very low flow nitrogen input (the nitrogen input is off at the beginning of the reaction). The reaction was heated to 110° C. The starting material quickly dissolved and Cs$_2$CO$_3$ (5 g, 16 mmols) was then added. A vigorous effervescence was observed and the nitrogen flow was connected. The reaction was stirred for 1 hour, emptying the Dean-Stark trap as necessary. HPLC-MS shows about 75% progress. Another 1 g of Cs$_2$CO$_3$ was added to the crude mixture and the reaction was stirred for an additional 1 hour. An HPLC-Ms shows >95% conversion. The crude reaction was then poured into 500 mL TBME and filtered through a 2"cake of silica. The solvents are removed under vacuum, and the resulting brown gum is re-dissolved in a 1:1 mix of TBME:hexanes, filtered over a 5 inch silica cake, and eluted with 2 L of the same solution. The organics were concentrated to dryness. The solids were dissolved in a 95:5 mix of hot heptane:TBME (c.a. 250 mL). The solution was then slowly cooled to 0° C. with stirring and seeded with solids from previous batches. A beige solid formed after 30 minutes. The slurry was left stirring at 0° C. for 2 hours. A pale beige solid was filtered (90 g, 83% yield), showed >99% purity by HPLC, and 85:15 ratio of double bond isomers. The remaining mother liquor was concentrated to an oil (c.a. 30 g) and was purified on a silica cartridge. (400 g, 10-100% TBME in hexanes over 12 CV, 100 ml/minute, ~254 nm). An additional 13 g of material is isolated. Analytical method: Xbridge phenyl column (250 mm×3.0 mm); 70% to 100% over 25 minutes, methanol with 0.1% TFA in water with 0.1% TFA, ~254 nm: 16.019 minutes (84.5% major isomer) and 16.439 minutes (14.9%, minor isomer). LC-MS method: Xbridge C18 column; 90% to 100% Acetonitrile/Methanol 1:1 with water; [546] Ms+~4.970 minutes, ~254 nm (single peak).

Preparation 5: Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate

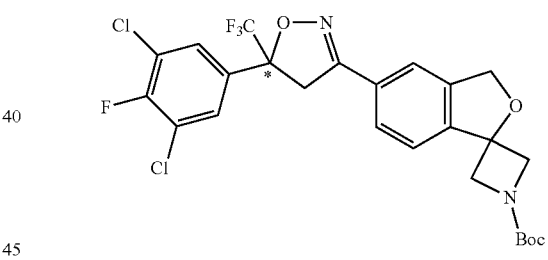

A solution of (Z)-tert-butyl 5'-(3-(3,5-dichloro-4-fluorophenyl)-4,4,4-trifluorobut-2-enoyl)-3'H-spiro[azetidine-3,1'-isobenzofuran]-1-carboxylate (Preparation 4, 1.0 g, 1.83 mmol) in dichloroethane (8 mL) was cooled to −2° C. The catalyst, (2S)-1-(acridin-9-ylmethyl)-2-((R)-hydroxy(6-methoxyquinolin-4-yl)methyl)-5-vinylquinuclidin-1-ium bromide (180 mg, 0.37 mmol) was added and stirred to dissolve. In a separate flask, 10N aqueous sodium hydroxide (0.42 mL) was cooled to 5° C. and 50 wt % aqueous hydroxylamine (254 mg, 3.84 mmol) was added and stirred for 10 minutes. This basic solution was added in one shot to the reaction solution. The resulting solution was stirred at 0° C. for 1 hour. The reaction mixture was washed with water (2×10 mL). The solution was concentrated to a volume of 3 mL and then 15 mL of methyl tert-butyl ether was added and the heterogeneous mixture was stirred at ambient temperature for 15 minutes. The precipitated catalyst was removed by filtration. The organic solution at this point contained a 90:10 mixture of isoxazoline enantiomers. The organics were concentrated to a volume of 3 mL and the product was allowed to slowly crystallize at ambient temperature and was then cooled to 0° C. The product was isolated by filtration to afford 910 mg (89%) of white crystals. The crystallization generally provided an enantiomeric upgrading such that the percentage of active isomer was >95%. Chiral LC: Chiralpak AD 250× 3.0 mm column, 70:30 hexane:ethanol (0.2% diethylamine), 1.0 mL/minute, 260 nm detection. Retention times: 5.4 minutes and 12.4 minutes. ¹H NMR, 600 MHz (CDCl₃) δ ppm: 7.70 (d, 1H), 7.60 (m, 4H), 5.18 (s, 2H), 4.36 (d, 2H), 4.15 (m, 3H), 3.72 (d, 1H), 1.55 (s, 9H). m/z 462 ([M+H]-Boc). The asterisk (*) depicts a chiral center.

Preparation 6: Chiral—5'-(5-(3,5-dichloro-4-fluorophenyl)-5-(trifluoromethyl)-4,5-dihydroisoxazol-3-yl)-3'H-spiro[azetidine-3,1'-isobenzofuran]hydrochloride

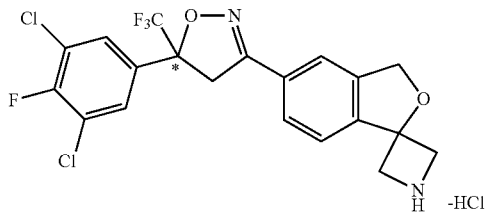

Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate (Preparation 5, 1.1 g, 2.0 mmol) was dissolved in methanol (50 mL). A methanolic solution of HCl (5 mL of a 1.25M solution) was added and the reaction was heated to 65° C. for 18 hours. The reaction was cooled and concentrated under vacuum to afford the intermediate (980 mg, 100%) a solid. ¹H NMR, 300 MHz (d₆-DMSO) δ ppm: 9.86 (1H), 9.45 (1H), 8.14 (1H), 7.82 (3H), 7.70 (1H), 5.15 (2H), 4.41-4.30 (6H); m/z (CI) 461 [M+H] (free amine). The asterisk (*) depicts a chiral center.

Preparation 7: Chiral-5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate

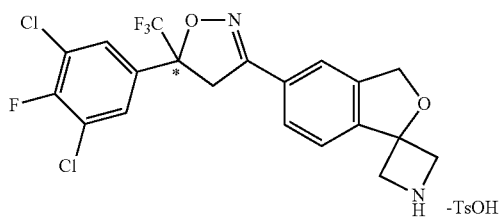

Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate (Preparation 29, 162 g, 289 mmol) was dissolved in ethanol (1800 mL) and water (200 mL). p-toluenesulfonic acid monohydrate (113 g, 577 mmol) was added and the solution was heated to 75° C. for 3 hours. The reaction was cooled to 20° C. and was filtered to isolate the product. The product was dried to afford 167.4 g (92%) of a white powder. ¹H NMR, 600 MHz (d₆-DMSO) δ ppm: 8.98 (br s, 2H), 7.92 (d, 1H), 7.80 (m, 3H), 7.70 (s, 1H), 7.50 (d, 2H), 7.15 (d, 2H), 5.15 (s, 2H), 4.40 (m, 6H), 2.25 (s, 3H); m/z (CI) 461 [M+H] (free amine). The asterisk (*) depicts a chiral center.

Preparation 8. Chiral-5'-(5-(3,5-dichloro-4-fluorophenyl)-5-(trifluoromethyl)-4,5-dihydroisoxazol-3-yl)-3'H-spiro[azetidine-3,1'-isobenzofuran]benzene sulfonate

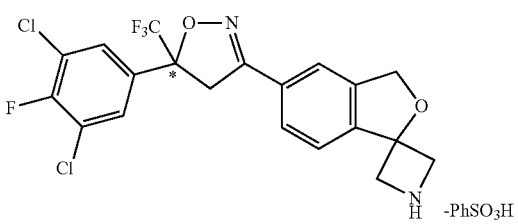 [SMILES: "-PhSO3H" ; Fc1c(Cl)cc(C2(C(F)(F)F)CC(c3ccc4c(c3)COC43CNC3)=NO2)cc1Cl]

Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate (Preparation 5, 80 g, 140 mmol) was dissolved in ethanol (280 mL). Benzenesulfonic acid (28.5 g, 178 mmol) was added and the solution was heated to 62° C. for 30 minutes. The reaction was cooled to 5° C. and was filtered to isolate the product. The product was dried to afford 81 g (92%) of a white powder. ¹H NMR, 600 MHz (d₆-DMSO) δ ppm: 9.10 (br s, 1H), 8.90 (br s, 1H) 7.95 (d, 1H), 7.82 (m, 3H), 7.70 (s, 1H), 7.62 (d, 2H), 7.34 (m, 3H), 5.13 (s, 2H), 4.35 (m, 6H); m/z (CI) 461 [M+H] (free amine). The asterisk (*) depicts a chiral center.

Example 1

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone

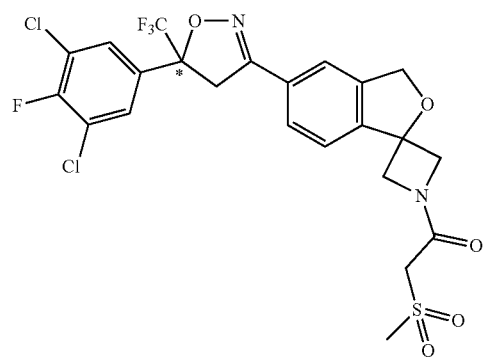 [SMILES: CS(=O)(=O)CC(=O)N1CC2(C1)OCc1cc(C3=NOC(c4cc(Cl)c(F)c(Cl)c4)(C(F)(F)F)C3)ccc12]

The p-toluenesulfonic acid salt of chiral-5'-(5-(3,5-dichloro-4-fluorophenyl)-5-(trifluoromethyl)-4,5-dihydroisoxazol-3-yl)-3'H-spiro[azetidine-3,1'-isobenzofuran] (Preparation 7,157 g, 248 mmol) was stirred as a slurry in methyl tert-butyl ether (700 mL) at ambient temperature. To this was added 0.5N aqueous sodium hydroxide (600 mL, 300 mmol) and the mixture was stirred for 15 minutes at which time the two layers were clear. The aqueous layer was separated and the organics were washed with saturated brine (200 mL) and dried with sodium sulfate (5 grams). The organics were filtered to remove the solids.

In a separate flask, 43.2 gm (297 mmol) of 2-methansulfonylacetic acid was dissolved in DMF (300 mL) at ambient temperature. Carbonyldiimidazole (45.1 gm, 271 mmol) was added portion wise to the solution over 15 minutes to control foaming. After addition, the solution was stirred for 15 minutes at ambient temperature. The above ethereal solution of the amine was added to this reaction in one portion. The resulting solution was stirred at ambient temperature for 30 minutes. Water (800 mL) was added to quench the reaction. After stirring for two minutes, the aqueous layer is settled and removed. The organic layer is stirred at ambient temperature for one hour. During this time, the racemate precipitated from the reaction mixture. The mixture is then filtered through filter aid (Celite 545) to remove the racemic material. The sulfonamide remaining in solution is greater than 99% of a single isomer (i.e., S). The organic solution is washed with water twice (2×1 L) and concentrated to an off-white solid, (109.5 gm, 76%). Residual color can be removed by dissolving material in ethanol, stirring with 10 wt % charcoal (Darco G-60), filtering, and concentrating to a solid. The asterisk (*) depicts a chiral center.

Alternatively, the besylate salt of the chiral 5'-(5-(3,5-dichloro-4-fluorophenyl)-5-(trifluoromethyl)-4,5-dihydroisoxazol-3-yl)-3'H-spiro[azetidine-3,1'-isobenzofuran] can be coupled with methanesulfonylacetic acid using n-propylphosphonic anhydride via a simplified one-pot process instead of the CDI two-pot method. Triethylamine (0.825 g, 1.3 eq.) was added drop-wise over 1 minute at about 18-22° C. to methanesulfonylacetic acid (0.615 g, 1.3 eq.) and chiral-5'-(5-(3,5-dichloro-4-fluorophenyl)-5-(trifluoromethyl)-4,5-dihydroisoxazol-3-yl)-3'H-spiro[azetidine-3,1'-isobenzofuran] (Preparation 8, 2.1 g, 3.39 mmol) in 9.3 mL ethyl acetate (EtOAc). The addition funnel was rinsed with 0.5 mL EtOAc and the resulting mixture stirred for a minimum of 2 hours and cooled to <10° C. To this mixture, 50% n-propylphosphonic anhydride in EtOAc (4.313 g, 2.0 eq) was added drop-wise over 15 minutes at <10° C. The addition funnel was then rinsed with 1.5 mL EtOAc. The reaction mixture was warmed to 35° C. and stirred overnight. (HPLC >97% with <1% starting material). To the reaction was added 1.0 g Celite filter aid and filtered through a 1 g celite plug in a 15 mL coarse frit glass funnel and rinsed with 4 mL EtOAc (2×). In process chiral HPLC was 98.8% S-enantiomer and 1.2% R-enantiomer; HPLC >97%. Filtrate was washed with 4 mL water (3×), 4 mL 10% $NH_4Cl$, 4 mL water and the organic layer concentrated to the amorphous S form of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (foam, 70-80% yield). $^1$H NMR, 600 MHz ($d_6$-CDCl3) δ ppm: 7.65 (m, 5H), 5.19 (br s, 2H), 4.70 (m, 2H), 4.48 (d, 1H), 4.38 (d, 1H), 4.12 (d, 1H), 3.90 (d, 2H), 3.72 (d, 1H), 3.23 (s, 3H); m/z (CI) 581 [M+H].

Example 2

Preparation of Crystal Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone—Crystallization of the Amorphous S-Enantiomer Originally, crystal Form A seeds were prepared by dissolving between 100 mg and 200 mg of the amorphous S form of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone in methanol at room temperature. A small aliquot of this solution was placed in an uncapped 4-mL glass vial. The 4-mL glass vial was placed inside a larger 20-mL amber vial containing several mL of diisopropyl ether and then the 20 mL vial was capped. The solvent vapors were allowed to evaporate/diffuse for a period of 5 days, at which time solids were noted. Examination of the solids under polarized light microscopy revealed highly birefringent crystalline particles. Analysis by hot stage microscopy demonstrated a melting point between 130 and 170° C. Further examination confirmed Form A (e.g., the seed crystals).

Crystal Form A can be prepared by charging 15.4 grams of the amorphous S-enantiomer described above, dissolved in 92 mL ethanol and 7.7 mL ethyl acetate, to a preheated 1-L jacketed reactor equipped with overhead stirring, temperature probe/readout, programmable chiller, nitrogen headspace purge, and water-cooled overhead condenser. Next, 54 mL of n-heptane is added. The resulting system is heated to 60° C. and a solution results. The solution is cooled to 45° C. over 15 minutes, and a hazy or milky solution results, without any signs of the formation of crystalline solids. 308 mg of crystalline Form A that was hand ground with a mortar and pestle is then added. The seeds persist in the reactor. The system is held at 45° C., then the contents of the reactor are cooled to 30° C. at 1.5° C. per hour linearly, then cooled to 10° C. over three hours linearly, then held at 10° C. for 4.5 hours. A white, stirrable slurry results. The slurry is cooled to 0-1° C. over 20 minutes and held overnight (about 23 hours) at 0-1° C. The contents of the reactor are transferred to a sintered glass filter and vacuum is applied until a solid cake is observed. The cake is washed on the filter with about 40 mL of 60% n-heptane/40% ethanol denatured with 0.5% toluene. The cake is further washed with approximately 300 mL n-heptane. The cake is dried with air by pulling vacuum for about 1 hour, then the cake is dried further in a vacuum oven overnight at 40° C. The resulting 9.26 grams of Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone were confirmed by DSC.

Alternatively, crystal Form A can be prepared by charging 4 grams of the amorphous S-enantiomer (isolated by rotavapping to a foam) to a 50-mL MultiMax reactor equipped with jacketed heating/cooling, overhead stirring, thermocouple, and a dispensing box. Add 24 mL of a solvent mixture consisting of 60 volume % ethanol (denatured with 0.5 volume % toluene), 35% heptane, and 5% ethyl acetate. Heat the mixture to 60° C., and a clear solution results. Cool to 45° C. over 20 minutes, then add seeds of crystalline Form A (approximately 40 mg). The seeds persist in the reactor vessel. Hold for 2 hours at 45° C., then cool to 20° C. over 12.5 hours (about 2° C./hour) linearly, then hold at 20° C. while adding heptane (16 mL) over 1 hour using the dispensing box. At this point, a white slurry has formed. Then hold 1 hour at 20° C., and subsequently cool to −10° C. over 10 hours and hold at −10° C. for 3 hours. Filter the resulting slurry on a pre-chilled, sintered glass filter, and then wash with 10 mL of 80% heptane/20% ethanol (denatured with 0.5 vol % toluene), pre-chilled to approximately 0° C. Dry the cake in the vacuum oven over 2.5 days at 30° C., absolute pressure about 150-160 torr with a nitrogen sweep. The resulting 3.45 grams of Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone obtained from the filter was confirmed by DSC.

Alternatively, crystal Form A can be prepared by charging the amorphous S form to a vial containing about 18 mL of diisopropyl ether, 1.1 mL methanol, and Form A seeds. The reaction mixture was stirred. The reaction mixture was heated and cooled from 40° C. to 2° C., with cooling over about 4 hours and heating over about 1 hour, for a duration of six heating and cooling cycles. The reaction mixture was held at about 1° C. for 1 day. The mixture was reheated from 1° C. to 55° C. and then cooled to about 25° C. over a period of about 3.3 hours (approximately 200 minutes), and then cooled again to about 1° C. over a period of about 1-hour. The mixture was held at room temperature for about 24 hours then cooled to about 1° C. over about 30 minutes. The reaction mixture was held at 1° C. for several hours. The solids were transferred to a sintered glass fritted funnel and washed with cyclohexane. The solids were vacuum dried.

Example 3

Preparation of Crystal Form of (R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone—Crystallization of the Amorphous R-Enantiomer The crystalline form can be prepared adding 50 mg of amorphous R-enantiomer from above to a 20-mL glass vial with diethyl ether. The sample was heated and sonicated in a sonicating bath for approximately 1 hour. The amorphous solids seemed to dissolve with heating/sonication, and then solids were observed to come back out of solution. Inspection of the solids by polarized light microscopy indicated very tiny particles that may be indicating birefringence (an indicator of crystallinity). The suspension was removed from the 20-mL glass vial and placed in a 15-mL sealed pressure tube with a PTFE (Teflon™)-coated magnetic stir bar. This tube was heated and cooled from 60° C. to −10° C. repeatedly over about 20 hours, a total of 5 heating/cooling cycles, heating over about 1 hour, cool over about 3 hours, with magnetic stirring. Examination of the resulting suspension by polarized light microscopy revealed much larger crystals than before the heating/cooling cycles. A small aliquot of the resulting solids were isolated from the suspension by filtration, dried at 30° C. under vacuum at approximately 160 torr absolute pressure overnight, and analyzed by PXRD, giving a diffraction pattern similar to Form A. The solids were also analyzed by DSC, and exhibited a broad melting point around 146° C. (peak endotherm).

HPLC Assay Methods

Chiral HPLC of the sulfonamide enantiomers approximately (90/10 (S/R)): Chiralpak IA column (250×3.0 mm), isocratic 50/50 methyl tert-butyl ether/ethanol with 0.2% diethylamine, flow rate 1.0 mL/minute, detection at 260 nm. Retention times: 8.5 minutes (S enantiomer) and 16.5 minutes (R enantiomer). The isolated solid is about 99% S and about 1% or less of the inactive isomer (R). Further enantiomeric enrichment can be obtained by stirring in MTBE (for example) and filtering any solids which form. Product was identical to the first eluting enantiomer of the racemate under the preparative chiral SFC conditions previously described.
$^1$H NMR, 600 MHz (d$_6$-DMSO): 7.88 (d, 2H), 7.82 (d, 1H), 7.73 (m, 2H), 5.18 (s, 2H), 4.62 (dd, 2H), 4.42 (dd, 2H), 4.28 (m, 4H), 3.20 (s, 3H); m/z (CI) 582 [M+H].

Additional Chiral HPLC Assay Method:

Chiracel AD-3R, 150×4.6 mm, 3 micron column. Flow rate of 1.5 mL per minute using a isocratic solvent mixture of 75:25 methanol:acetonitrile. Column temperature 40° C. Detection at 260 nm. Elution times are: S-isomer (4.0 minutes), R-isomer (7.8 minutes). Run time 15 minutes.

HPLC Assay Method for the S-Isomer:

ACE Excel 2 C18-AR, 150×4.6 mm column. Column temperature of 50° C. Detection at 260 nm. Flow rate is 1.5 mL per minute. Mobile phase A: 0.1% trifluoroacetic acid in water. Mobile phase B: 0.1% TFA in acetonitrile. Run at a gradient: initial time 45% B, 4.5 minutes 55% B, 20 minutes 100% B. Elution time of S-isomer is 9.8 minutes.

What is claimed is:

1. A crystalline Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone which exhibits at least one of the following properties:
   a) an X-ray diffraction pattern having characteristic peaks expressed in degrees 2θ (±0.2°) at about 17.18, 18.83, and 20.07;
   b) an X-ray diffraction pattern having characteristic peaks expressed in degrees 2θ (±0.2°) at about 17.18, 18.83, and 20.07, and further comprising at least one additional diffraction peak expressed in degrees 2θ (±0.2°) selected from the group consisting of peaks at about 4.70, 9.39, 14.10, 15.70, 19.12, 20.97, 21.42, 22.03, 22.54, 23.62, and 28.42;
   c) an X-ray diffraction pattern having characteristic peaks expressed in degrees 2θ (±0.2°) at about 17.18, 18.83, and 20.07, and further comprising at least one additional diffraction peak expressed in degrees 2θ (±0.2°) at about 21.42, 22.54, and 28.42;
   d) an X-ray diffraction pattern having characteristic peaks expressed in degrees 2θ (±0.2°) at about 17.18, 18.83, 20.07, 21.42, 22.54, and 28.42;
   e) a Fourier Transform infrared spectrum at the 1800 to 600 cm$^{-1}$ range, substantially as shown in FIG. 2;
   f) a differential scanning calorimeter thermogram having a single predominant endotherm at about 145.53° C. at a scan rate of 10° C. per minute, substantially as shown in FIG. 3.1; and
   g) a differential scanning calorimeter thermogram having a single predominant endotherm within the range of 144.01 to 146.92° C. at a scan rate of 10° C. per minute, substantially as shown in FIG. 3.2.

2. The crystalline form of claim 1 which exhibits
   (i) at least one of the following X-ray diffraction patterns selected from:
      a) an X-ray diffraction pattern having characteristic peaks expressed in degrees 2θ (±0.2°) at about 17.18, 18.83, and 20.07;
      b) an X-ray diffraction pattern having characteristic peaks expressed in degrees 2θ (±0.2°) at about 17.18, 18.83, and 20.07, and further comprising at least one additional diffraction peak expressed in degrees 2θ (±0.2°) at about 21.42, 22.54, and 28.42;
      c) an X-ray diffraction pattern having characteristic peaks expressed in degrees 2θ (±0.2°) at about 17.18, 18.83, 20.07, 21.42, and 28.42; and
   (ii) a Fourier Transform infrared spectrum at the 1800 to 600 cm$^{-1}$ range, substantially as shown in FIG. 2; or
   (iii) a differential scanning calorimeter thermogram having a single predominant endotherm at about 145.53° C. at a scan rate of 10° C. per minute, substantially as shown in FIG. 3.1 or the differential scanning calorimeter thermogram having a single predominant endotherm within the range of 144.01 to 146.92° C. at a scan rate of 10° C. per minute, substantially as shown in FIG. 3.2.

3. The crystalline form of claim 1 which exhibits the following properties:
   a) an X-ray diffraction pattern having characteristic peaks expressed in degrees 2θ (±0.2°) at about 17.18, 18.83, and 20.07, and further comprising at least one additional diffraction peak expressed in degrees 2θ (±0.2°) at about 4.70, 9.39, 14.10, 15.70, 19.12, 20.97, 21.42, 22.03, 22.54, 23.62, and 28.42; and
   b) a Fourier Transform infrared spectrum at the 1800 to 600 cm$^{-1}$ range, substantially as shown in FIG. 2.

4. The crystalline form of claim 1 which exhibits the following properties:
   a) an X-ray diffraction pattern having characteristic peaks expressed in degrees 2θ (±0.2°) at about 17.18, 18.83, and 20.07, and further comprising at least one additional diffraction peak expressed in degrees 2θ (±0.2°) at about 4.70, 9.39, 14.10, 15.70, 19.12, 20.97, 21.42, 22.03, 22.54, 23.62, and 28.42; and
   b) a differential scanning calorimeter thermogram having a single predominant endotherm at about 145.53° C. at a scan rate of 10° C. per minute, substantially as shown in FIG. 3.1 or the differential scanning calorimeter thermogram having a single predominant endotherm within the range of 144.01 to 146.92° C. at a scan rate of 10° C. per minute, substantially as shown in FIG. 3.2.

5. The crystalline form of claim 1 which exhibits the following properties:
   a) a Fourier Transform infrared spectrum at the 1800 to 600 cm$^{-1}$ range, substantially as shown in FIG. 2; and
   b) a differential scanning calorimeter thermogram having a single predominant endotherm at about 145.53° C. at a scan rate of 10° C. per minute, substantially as shown in FIG. 3.1 or the differential scanning calorimeter thermogram having a single predominant endotherm within the range of 144.01 to 146.92° C. at a scan rate of 10° C. per minute, substantially as shown in FIG. 3.2.

6. The crystalline form of claim 1 which exhibits an X-ray diffraction pattern having characteristic peaks expressed in degrees 2θ (±0.2°) at about 17.18, 18.83, 20.07, and further comprising at least one additional diffraction peak expressed in degrees 2θ (±0.2°) at about 21.42, 22.54, and 28.42.

7. The crystalline form of claim 1 which exhibits a Fourier Transform infrared spectrum at the 1800 to 600 cm$^{-1}$ range, substantially as shown in FIG. 2.

8. The crystalline form of claim 1 which exhibits a differential scanning calorimeter thermogram having a single predominant endotherm at about 145.53° C. at a scan rate of 10° C. per minute, substantially as shown in FIG. 3.1, or the differential scanning calorimeter thermogram having a single predominant endotherm within the range of 144.01 to 146.92° C. at a scan rate of 10° C. per minute, substantially as shown in FIG. 3.2.

9. A composition comprising a therapeutically effective amount of crystalline Form A, amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, or the crystalline racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or any mixture thereof, and a pharmaceutically or veterinarily acceptable excipient, diluent, carrier, or mixture thereof.

10. The composition of claim 9, further comprising abamectin, selamectin, moxidectin, ivermectin, emamectin, doramectin, eprinomectin, pyrantel, amitraz, albendazole, cambendazole, fenbendazole, flubendazole, mebendazole, febantel, octadepsipeptides, oxfendazole, oxibendazole, paraherquamide, parbendazole, praziquantel, thiabendazole, tetramisole, triclabendazole, levamisole, oxantel, novaluron, morantel, milbemycin, milbemycin oxime, demiditraz, diethylcarbamazine, fipronil, hydroprene, kinoprene, methoprene, metaflumizone, niclosamide, permethrin, pyrethrins, pyriproxyfen, spinosad, aminoacetonitrile derivative(s), or any mixture thereof.

11. A method of treating a parasitic infection or infestation in an animal, comprising administering to the animal in need thereof, a therapeutically effective amount of a compound of crystalline Form A, amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, prepared from crystalline Form A, or the crystalline racemate of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)-ethanone, or any mixture thereof.

12. The method of claim 11, further comprising administering at least one additional veterinary agent selected from abamectin, selamectin, moxidectin, ivermectin, emamectin, doramectin, eprinomectin, pyrantel, amitraz, albendazole, cambendazole, fenbendazole, flubendazole, mebendazole, febantel, octadepsipeptides, oxfendazole, oxibendazole, paraherquamide, parbendazole, praziquantel, thiabendazole, tetramisole, triclabendazole, levamisole, oxantel, novaluron, morantel, milbemycin, milbemycin oxime, demiditraz, diethylcarbamazine, fipronil, hydroprene, kinoprene, methoprene, metaflumizone, niclosamide, permethrin, pyrethrins, pyriproxyfen, spinosad, aminoacetonitrile derivative(s), or any mixture thereof.

13. The method of claim 11 or 12, wherein the animal is a companion animal or livestock and administration is oral, topical, or by injection.

14. A process for preparing crystalline Form A comprising:
   a) charge amorphous (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone solids to a solvent;
   b) heat the mixture to about 60° C.;
   c) cool the mixture to about 45° C.;
   d) add Form A seeds and hold at about 45° C.;
   e) slowly cool the mixture; and
   f) filter, wash, and dry the solids.

15. The process of claim 14 wherein the solvent contains about 60% ethanol, about 5% ethyl acetate, and about 35% n-heptane.

16. The process of claim 15 wherein the mixture is cooled from about 60° C. to about 45° C. over a period of about 15 to 20 minutes, Form A seeds are added, hold the mixture at 45° C. for about 2 hours then linearly cooled to 10° C., and held at 10° C. for about 4.5 hours, cooled further to 0-1° C. and held at 0-1° C. for about 23 hours to obtain a slurry.

17. The process of claim 16 wherein the slurry is filtered under vacuum and the solids washed with a solution comprising n-heptane and ethanol, and the solids dried further under vacuum to obtain the resultant Form A.

18. The method of claim 12 wherein the at least one additional veterinary agent is selamectin.

19. The method of claim 12 wherein the at least one additional veterinary agent is selected from moxidectin or pyrantel, or mixture thereof.

20. The method of claim 11 wherein the animal is a companion animal.

* * * * *